US010842444B2

(12) United States Patent
Hoeng et al.

(10) Patent No.: US 10,842,444 B2
(45) Date of Patent: Nov. 24, 2020

(54) SYSTEMS AND METHODS FOR EVALUATING PERTURBATION OF XENOBIOTIC METABOLISM

(71) Applicant: Philip Morris Products S.A., Neuchatel (CH)

(72) Inventors: Julia Hoeng, Corcelles (CH); Manuel Claude Peitsch, Peseux (CH)

(73) Assignee: Philip Morris Products S.A., Neuchâtel (CH)

( * ) Notice: Subject to any disclaimer, the term of this patent is extended or adjusted under 35 U.S.C. 154(b) by 626 days.

(21) Appl. No.: 14/914,786

(22) PCT Filed: Sep. 4, 2014

(86) PCT No.: PCT/EP2014/068889
§ 371 (c)(1),
(2) Date: Feb. 26, 2016

(87) PCT Pub. No.: WO2015/036320
PCT Pub. Date: Mar. 19, 2015

(65) Prior Publication Data
US 2016/0213328 A1 Jul. 28, 2016

Related U.S. Application Data

(60) Provisional application No. 61/877,612, filed on Sep. 13, 2013.

(51) Int. Cl.
*G01N 33/48* (2006.01)
*G01N 33/50* (2006.01)
*A61B 5/00* (2006.01)
*G16B 50/00* (2019.01)
*G16C 20/10* (2019.01)
*A61B 5/08* (2006.01)
*G16B 5/00* (2019.01)

(52) U.S. Cl.
CPC .............. *A61B 5/7264* (2013.01); *A61B 5/08* (2013.01); *A61B 5/4866* (2013.01); *A61B 5/4884* (2013.01); *A61B 5/7246* (2013.01); *G16B 50/00* (2019.02); *G16C 20/10* (2019.02); *G16B 5/00* (2019.02)

(58) Field of Classification Search
None
See application file for complete search history.

(56) References Cited

U.S. PATENT DOCUMENTS

| 8,417,661 B2 | 4/2013 | Thomson et al. |
| 9,558,318 B2 | 1/2017 | Hoeng et al. |
| 9,815,048 B2 | 11/2017 | Chandler et al. |

FOREIGN PATENT DOCUMENTS

| JP | 2009-529329 A | 8/2009 |
| WO | WO 2012/168483 A1 | 12/2012 |
| WO | WO 2013034300 | 3/2013 |
| WO | WO 2013/190083 A1 | 12/2013 |

OTHER PUBLICATIONS

Thompson et al., (Toxicology and Applied Pharmacology. Aug. 8, 2013 .272(3):863-878 and Supplementary Section (42 pages total). (Year: 2013).*
Thomson et al., "Quantitative assessment of biological impact using transcriptomic data and mechanistic network models," Toxicology and Applied Pharmacology, 272:863-878 and 26 pages of Supplemental Information (2013).
Iskandar et al., "Systems approaches evaluating the perturbation of xenobiotic metabolism in response to cigarette smoke exposure in nasal and bronchial tissues," BioMed Research International, vol. 2013, 16 pages (2013).
Anonymous: Reverse casual reasoning methods whitepaper, Internet citation, Feb. 4, 2011, Retrieved from the Internet: URL:http://www.selventa.com/attachments/whitepapersjreverse-causal-reasoning.pdf [retrieved on Aug. 17, 2012] (26 pages).
Hoeng et al., "Chapter 7: Toxicopanomics: Applications of Genomics, Transcriptomics, Proteomics, and Lipidomics in Predictive Mechanistic Toxicology," Hayes' Principles and Methods of Toxicology (Sixth Edition), pp. 295-332 (2014).
International Search Report and Written Opinion for PCT/EP2014/068889 dated Dec. 8, 2014.
Sridhar et al., "Smoking-induced gene expression changes in the bronchial airway are reflected in nasal and buccal epithelium," BMC Genomics, vol. 9, No. 1 (Jan. 1, 2008) , 13 pages.
X. Zhang et al., "Similarities and differences between smoking-related gene explosion in nasal and bronchial epithelium," Physiological Genomics, vol. 41, No. 1 (Mar. 3, 2010), pp. 1-8.
Hoeng et al., "Case study: the role of mechanistic network models in systems toxicology," Drug Discovery Today, vol. 19, No. 2 (Feb. 1, 2014), pp. 183-192.
Japanese Decision to Grant a Patent issued in Japanese Patent Application No. 2016-541887, dated Jul. 9, 2019, 2 pages.

(Continued)

*Primary Examiner* — Russell S Negin
(74) *Attorney, Agent, or Firm* — Sterne, Kessler, Goldstein & Fox, P.L.L.C.

(57) ABSTRACT

Systems and methods are provided for assessing perturbation of a target biological tissue caused by exposure to an agent. A set of scores indicative of a perturbation of the target biological tissue is determined based on a set of contrast data and a computational causal network model of xenobiotic metabolism in the target biological tissue and a surrogate biological tissue. The contrast data includes differences between activity measures of measurable nodes obtained from the surrogate biological tissue while exposed to the agent, and while exposed to a control. To determine the set of scores, a set of values is computed that indicates a perturbation of the surrogate biological tissue caused by the agent. A correlation is identified between the set of values for the backbone nodes obtained from the surrogate biological tissue and the set of scores that is indicative of a perturbation of the target biological tissue.

16 Claims, 21 Drawing Sheets

(56) References Cited

OTHER PUBLICATIONS

Jennifer Beane et al., "Reversible and permanent effects of tobacco smoke exposure on airway epithelial gene expression", Genome Biology 2007, vol. 8, No. 9, Article R201, Sep. 25, 2007, pp. 1-17.
Yohan Bosse et al., "Molecular Signature of Smoking in Human Lung Tissues", American Association for Cancer Research Journals, Jun. 1, 2012, pp. 3753-3764.
Xinxin Ding et al., "Human Extrahepatic Cytochromes P450: Function in Xenobiotic Metabolism and Tissue-Selective Chemical Toxicity in the Respiratory and Gastrointestinal Tracts", Annual Review of Pharmacology and Toxicology, vol. 43, pp. 149-173 (Volume publication dated Apr. 2003).
Stephan Gebel et al., "The Kinetics of Transcriptomic Changes Induced by Cigarette Smoke in Rat Lungs Reveals a Specific Program of Defense, Inflammation, and Circadian Clock Gene Expression", Toxicology Sciences vol. 93, No. 2, Jul. 23, 2006, pp. 422-431.
Robert Gentleman et al., "Bioinformatics and Computational Biology Solutions using R and Bioconductor", Aug. 5, 2005, pp. 1-36.
Song Huang et al., "The Use of In Vitro 3D Cell Models in Drug Development for Respiratory Diseases", Drug Discovery and Development—Present and Future, Dr. Izet M. Kapetanovic, InTech, DOI: 10.5772/28132, Available from: https://www.intechopen.com/books/drug-discovery-and-development-present-and-future/the-use-of-in-vitro-3d-cell-models-in-drug-development-for-respiratory-diseases.
Rafael A. Irizarry et al., "Exploration, normalization, and summaries of high density oligonucleotide array probe level data", Biostatistics (2003) vol. 4, No. 2, pp. 249-264.
Philip H. Karp, et al., "An In Vitro Model of Differentiated Human Airway Epithelia", Epithelial Cell Culture Protocols, Methods in Molecular Medicine, Humana Press Inc. 2002, vol. 188, pp. 115-137.
Carole Mathis et al., "Human bronchial epithelial cells exposed in vitro to cigarette smoke at the air-liquid interface resemble bronchial epithelium from human smokers", American Journal of Physiology—Lung Cellular and Molecular Physiology, vol. 304, Jan. 24, 2013, pp. L489-L503.
Heather Maunders et al., "Human bronchial epithelial cell transcriptome: gene expression changes following acute exposure to whole cigarette smoke in vitro", American Journal of Physiology—Lung Cellular and Molecular Physiology, vol. 292, Jan. 3, 2007, pp. L1248-L1256.
Simons Parrinello et al., "Stromal-epithelial interactions in aging and cancer: senescent fibroblasts alter epithelial cell differentiation", Journal of Cell Science, vol. 118, No. 3, 2005, pp. 485-496.
Alejandro A. Pezzulo et al., "The air-liquid interface and use of primary cell cultures are important to recapitulate the transcriptional profile of in vitro airway epithelia", American Journal of Physiology—Lung Cellular and Molecular Physiology, vol. 300, Oct. 21, 2010, pp. L25-L31.
The R Development Core Team, Reference Index, "R: A Language and Environment for Statistical Computing", Foundation for Statistical Computing, Version 2.6.2 (Feb. 2, 2008), pp. 1-2,673.
Frank Schembri et al., "MicroRNAs as modulators of smoking-induced gene expression changes in human airway epithelium", Proceedings of the National Academy of Sciences of the United States of America (PNAS), vol. 106, No. 7, Feb. 17, 2009, pp. 2319-2324.
Katrina Steiling et al., "The Field of Tissue Injury in the Lung and Airway", American Association for Cancer Research, Cancer Prevention Research 2008 vol. 1, Issue 6, Nov. 2008, pp. 396-403.
Lucie Stejskalova et al., "Acyl Hydrocarbon Receptor and Aryl Hydrocarbon Nuclear Translocator Expression in Human and Rat Placentas and Transcription Activity in Human Trophoblast Cultures", Toxicological Sciences, vol. 123, No. 1, May 31, 2011, pp. 26-36.
Yael Strulovici-Barel et al., "Threshold of Biologic Responses of the Small Airway Epithelium to Low Levels of Tobacco Smoke", American Journal of Respiratory and Critical Care Medicine, vol. 182, Aug. 6, 2010, pp. 1524-1532.
Aravind Subramanian, et al., "Gene set enrichment analysis: A knowledge-based approach for interpreting genome-wide expression profiles", Proceedings of the National Academy of Sciences of the United States of America (PNAS), vol. 102, No. 43, Oct. 25, 2005, pp. 15545-15550.
European Communication pursuant to Article 94(3) issued in related European Patent Application No. 14772296.1, dated Jan. 31, 2020, 5 pages.

\* cited by examiner

900

902 STORE DATA REPRESENTATIVE OF A COMPUTATIONAL CAUSAL NETWORK MODEL OF XENOBIOTIC METABOLISM

904 RECEIVE A SET OF CONTRAST DATA CORRESPONDING TO A DIFFERENCE BETWEEN TREATMENT DATA AND CONTROL DATA, THE TREATMENT DATA BEING REPRESENTATIVE OF A RESPONSE OF A SAMPLE OF SURROGATE BIOLOGICAL TISSUE TO EXPOSURE TO AN AGENT

906 DETERMINE ACTIVITY VALUES FOR AT LEAST SOME OF THE BACKBONE NODES BASED ON THE BIOLOGICAL ACTIVITY MEASURES OF AT LEAST SOME OF THE MEASURABLE NODES AND THE COMPUTATIONAL CAUSAL NETWORK MODEL

908 COMPUTE A SCORE INDICATING A PERTURBATION OF THE SAMPLE OF THE SURROGATE BIOLOGICAL TISSUE IN RESPONSE TO EXPOSURE TO THE AGENT

910 IDENTIFY A CORRELATION BETWEEN THE PERTURBATION OF THE TARGET BIOLOGICAL TISSUE IN RESPONSE TO THE AGENT AND THE PERTURBATION OF THE SURROGATE BIOLOGICAL TISSUE IN RESPONSE TO THE AGENT

912 PROVIDE THE SCORE TO INDICATE THE PERTURBATION OF THE TARGET BIOLOGICAL TISSUE IN RESPONSE TO THE AGENT

FIG. 9

SYSTEMS AND METHODS FOR EVALUATING PERTURBATION OF XENOBIOTIC METABOLISM

REFERENCE TO RELATED APPLICATIONS

This application is a U.S. Nationalization of PCT Application Number PCT/EP2014/068889 filed Sep. 4, 2014, which claims priority under 35 U.S.C. § 119 to U.S. Provisional Patent Application 61/877,612, entitled "Systems and Methods for Evaluating Perturbation of Xenobiotic Metabolism," filed Sep. 13, 2013, both of which are incorporated herein in their entireties.

BACKGROUND

Mammals, including humans, are equipped with sophisticated mechanisms to process carcinogens and other xenobiotic compounds. In studies assessing the effects of cigarette smoke (CS) exposure, a particular interest is given to xenobiotic metabolism, a mechanism by which an organism processes xenobiotic substances. In particular, xenobiotic metabolism includes a set of metabolic pathways that transform xenobiotic substances by altering their chemical structures and ultimately detoxifying them.

The metabolism of xenobiotic substances consists mainly of three phases: modification, conjugation, and excretion. During the modification phase, phase I enzymes convert lipophilic compounds into their hydrophilic forms in a set of oxidative reactions. The expression of a prominent phase I enzyme (cytochrome P450s, or CYPs) in a specific tissue may provide an indication of the tissue-specific consequences in cellular toxicology and organ pathology. In the conjugation phase, phase II enzymes catalyze conjugation reactions, such as glucuronidation, sulfation, methylation, and acetylation, which lead to detoxification of xenobiotic compounds. Finally, in the excretion phase, a phase III membrane transporter operates to excrete xenobiotic metabolites across cellular membranes to the exterior.

Although the liver is known to be the main organ responsible for the metabolism of xenobiotics, the liver mainly processes toxicants that are present in blood, which are absorbed through the digestive tract. Consequently, toxicants that enter the body via breathing bypass the liver detoxification mechanisms. CS generates a range of tissue injury and changes in the respiratory tract that precede the development of CS-associated lung diseases. Therefore, the lung and respiratory tract are important for studying the effects of CS toxicants. Many lung cell types, including bronchial epithelial cells, Clara cells, type II pneumocytes, and alveolar macrophages are capable of metabolizing xenobiotic compounds [Ding X, Kaminsky L S: Human extrahepatic cytochromes P450: Function in Xenobiotic Metabolism and Tissue-Selective Chemical Toxicity in the Respiratory and Gastrointestinal Tracts*. *Annual review of pharmacology and toxicology* 2003, 43(1):149-173.]. While lung cells and tissues from the respiratory tract may be instrumental to the study of xenobiotic metabolism, it is generally challenging to obtain a sample of the desired cells or tissues. The present disclosure provides systems and methods that address these challenges.

SUMMARY

The computer systems and computer program products described herein implement methods for assessing a perturbation of a target biological tissue, particularly when direct measurements from the target biological tissue are difficult to obtain. The target biological tissue is of mammalian origin, and the perturbation is caused by exposure to an agent. A set of scores indicative of a perturbation of the target biological tissue is determined based on a set of contrast data and a computational causal network model of the xenobiotic metabolism operating in both the target biological tissue and a surrogate biological tissue. The computational causal network model includes measurable nodes and backbone nodes connected by edges, where the backbone nodes and measurable nodes, each representing a biological activity, are related to xenobiotic metabolism. The edges represent causal relationships between connected nodes, where an activity value of a respective backbone node can be inferred from and is determined effectively by activity measures of the measurable nodes that are connected to the respective backbone node. The set of contrast data includes differences between (i) the activity measures of the measurable nodes obtained from a sample of the surrogate biological tissue that is exposed to the agent, and (ii) the activity measures of the measurable nodes obtained from a sample of the surrogate biological tissue that is exposed to a control. The set of scores is determined by computing a set of values for the backbone nodes using the set of contrast data, where the set of values for the backbone nodes indicates a perturbation of the surrogate biological tissue caused by the agent. To assess the perturbation of the target biological tissue, a correlation between the set of values for the backbone nodes obtained from the surrogate biological tissue and the set of scores that is indicative of a perturbation of the target biological tissue is identified.

In certain implementations, the set of scores is determined by providing data representative of the computational causal network model of xenobiotic metabolism stored in a memory unit, and receiving the set of contrast data obtained from samples of surrogate biological tissues exposed to the agent or the control. In certain implementations, the set of scores is determined by (i) measuring expression levels of the genes corresponding to the measurable nodes, the expression levels being the activity measures of the measurable nodes obtained from the sample of the surrogate biological tissue exposed to the agent or the control, and (ii) computing the differences between (a) the activity measures of the measurable nodes obtained from the sample of the surrogate biological tissue that is exposed to the agent, and (b) the activity measures of the measurable nodes obtained from the sample of the surrogate biological tissue that is exposed to the control. In certain implementations, the set of scores is determined by identifying a correlation between the set of scores for the backbone nodes obtained from the surrogate biological tissue and a set of scores for the backbone nodes obtained from the target biological tissue. It is not required that the scores for the backbone nodes obtained from the target biological tissue be determined after a correlation has been established. In certain implementations, the set of scores is determined by using the correlation and the set of scores for the backbone nodes obtained from the surrogate biological tissue to infer the set of scores that indicates perturbation of the target biological tissue.

In certain implementations, the computational causal network model of xenobiotic metabolism is represented by data which comprises, consists essentially of, or consists of the BEL statements as shown in Table 2. In certain implementations, the values for the backbone nodes indicating a perturbation of the surrogate biological tissue caused by the agent are network perturbation amplitude scores (NPA scores), scores provided by ingenuity pathway analysis (IPA), or scores provided by gene set enrichment analysis (GSEA).

In certain implementations, the perturbation of the target biological tissue occurs in vivo and the surrogate biological tissue is an in vitro culture of cells of the target biological tissue. The in vitro culture of cells of the target biological tissue can in certain implementations be an organotypic cell culture. In certain implementations, the target biological tissue comprises epithelial cells of the lower respiratory tract and the surrogate biological tissue comprises epithelial cells of the upper respiratory tract. In particular, the target biological tissue may comprise epithelial cells selected from the group consisting of epithelial cells derived respectively from lung, bronchus, primary bronchi, secondary bronchi, tertiary bronchi, bronchioles, trachea, nasal cavity, buccal cavity, and gingiva. In certain implementations, the surrogate biological tissue comprises epithelial cells selected from the group consisting of epithelial cells derived respectively from lung, bronchus, primary bronchi, secondary bronchi, tertiary bronchi, bronchioles, trachea, nasal cavity, buccal cavity, and gingiva. In certain implementations, the target biological tissue is more difficult to access or obtain than the surrogate biological tissue due to its anatomical location in the body. In certain implementations, the agent is selected from the group consisting of: cigarette smoke, carbon monoxide, soot, diesel exhaust particles, particulate matter, and air pollution. As shown in Table 1, particulate matter may be defined in accordance with EPA standards as a mixture of solid particles and liquid droplets found in the air. In particular, particulate matter may include "inhalable coarse particles" with diameters larger than 2.5 micrometers and smaller than 10 micrometers, "fine particles" with diameters less than 2.5 micrometers, or both. In an example, particulate matter includes an airborne pollutant that may be inhaled by a subject. In this case, the particulate matter may include tobacco smoke, cigarette smoke (CS), an aerosol including nicotine, an aerosol generated by heating tobacco, an aerosol generated by heating without combusting tobacco, carbon monoxide, soot, exhaust caused by combusting any hydrocarbon fuel, gasoline exhaust, diesel exhaust, coke oven emissions, or any suitable combination thereof.

In certain implementations, at least one value in the set of values for the backbone nodes that are determined using the set of contrast data corresponds to a transcriptional activity of an aryl hydrocarbon receptor (AHR). In particular, the backbone node that corresponds to AHR may have causal relationships with at least the seventeen measurable nodes that are listed in Table 1 as having a causal relationship with the backbone node AHR, and wherein a directionality of each of the causal relationships is listed in Table 1. In general, at least some of the backbone nodes, measurable nodes, and edges in the computational causal network model of xenobiotic metabolism correspond to the exemplary backbone nodes, the exemplary measurable nodes, and the causal relationships that are listed in Table 1.

In certain implementations, the correlation is identified by determining that the computational causal network model of xenobiotic metabolism is applicable to both the perturbation of the target biological tissue in response to the agent and the perturbation of the surrogate biological tissue in response to the agent. In certain implementations, at least one score in the set of scores is modified to generate a modified score, the modifying based on the identified correlation. In particular, modifying the score may include scaling the score by a scalar factor determined from the identified correlation. In certain implementations, the agent includes air pollutants, the surrogate biological tissue is sampled from nasal tissue, and the target biological tissue is lung tissue. In certain implementations, at least one score in the set of scores is a quadratic function of the activity measures for the at least some of the measurable nodes.

BRIEF DESCRIPTION OF THE DRAWINGS

Further features of the disclosure, its nature and various advantages, will be apparent upon consideration of the following detailed description, taken in conjunction with the accompanying drawings, in which like reference characters refer to like parts throughout, and in which:

FIG. 9 is a flow diagram of a method for evaluating the perturbation of a xenobiotic metabolism network model.

DETAILED DESCRIPTION

Figure 1:
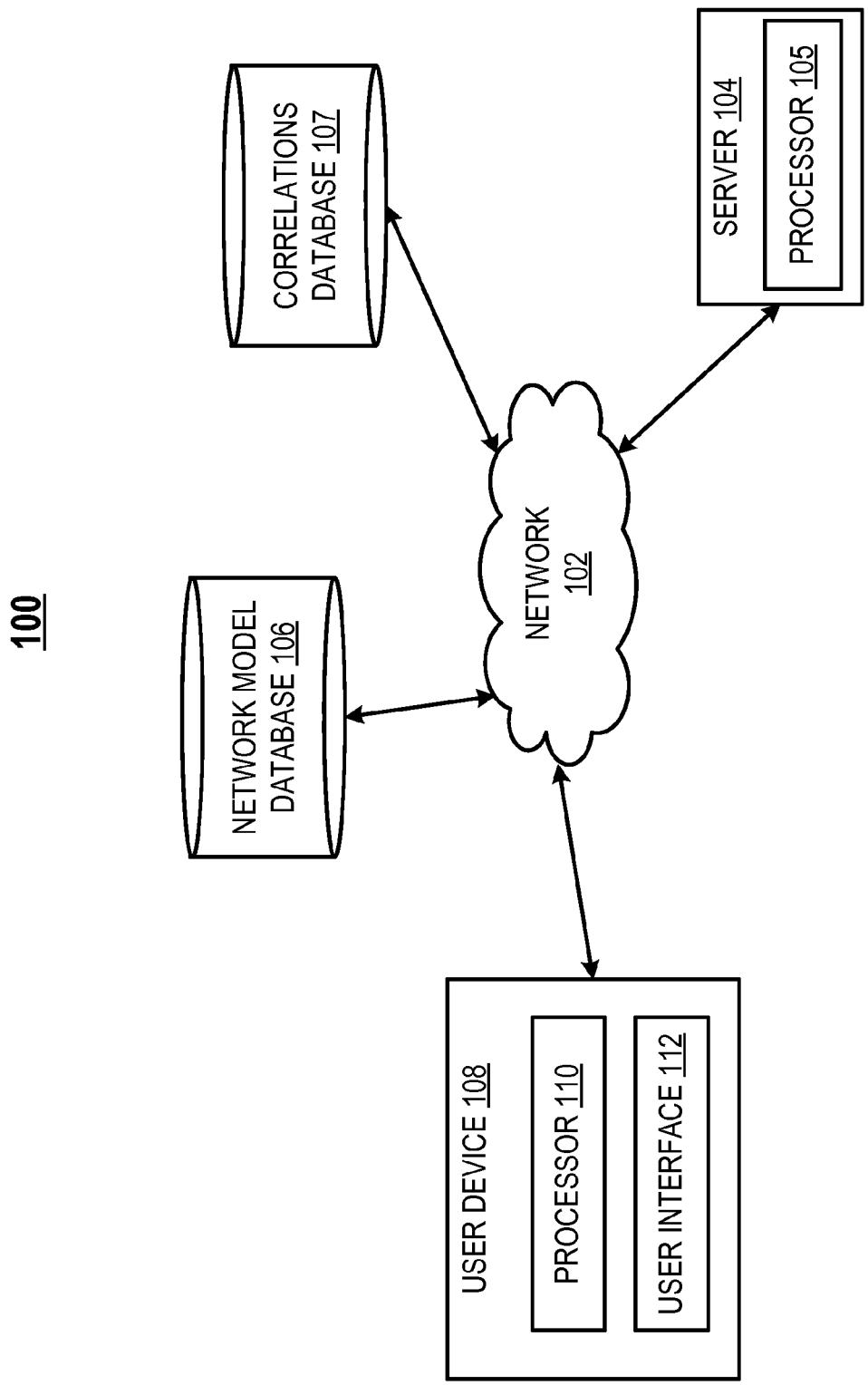
FIG. 1 depicts an exemplary system of a computer network and database structure for performing evaluating of a perturbation of a xenobiotic metabolism network model.

Described herein are computational systems and methods that can be used for determining the response of a biological system to a substance using a network model of xenobiotic metabolism. Advantageously, the systems and methods can be used to assess the effect of exposure to various substances of one type of tissue, a target tissue such as but not limited to tissues of the lower respiratory tract, using exposure data collected from a corresponding second type of tissue, a surrogate tissue such as but not limited to nasal tissue.

A computational causal network model is provided which is representative of certain aspects of a biological system. The model may be presented as a mathematical graph that includes nodes (also known as vertices) and edges. The nodes include "backbone nodes" and "measurable nodes." As used herein, backbone nodes represent biological processes or key actors in a biological process that are abstractions of certain functional mechanisms of the biological system, particularly those actors or processes that enable a feature of interest in the functioning of the biological system. In an example, the backbone nodes represent biological activities of various entities within the biological system, such as but not limited to, activities of compounds, DNA, RNA, proteins, peptides, antibodies, cells, tissues, and organs. Many of the activities corresponding to the backbone nodes are not measured but are inferred from the activities of the measureable nodes. Measurable nodes represent measurable activity levels of one or more biological entities that are known to be causally related by a backbone node. In an example, the measurable nodes represent gene expression levels. The activity of a backbone node may stimulate or inhibit the activity of a measurable node as represented by some of the edges. In the model, the edges may represent causal relationships between backbone nodes, as well as causal relationships between backbone nodes and each of their corresponding measurable nodes.

The measurable nodes represent the biological activities of various biological entities that can be measured by methods well known in the art, particularly high-throughput methods. The biological activities of the measurable nodes are referred to as biological activity measures. In an example, biological activity measures include differential gene expression levels of a set of genes, the activities of which are measured from a biological sample. The differential gene expression levels may be obtained from a set of contrast data that is representative of a difference between treatment data and control data. The treatment data corresponds to a response of a set of biological entities in a sample to an agent, while the control data correspond to the response of the same biological entities under control conditions, for example, the absence of the agent.

An edge in the network model represents a directional relationship from a backbone node to a measurable node or a directional relationship between two backbone nodes. The activity of a backbone node may be considered to be stimulated or inhibited as a consequence of the changes of the measurable nodes. This is reflected by the causal relationships represented by the edges that connect the backbone node to the measurable nodes. In the xenobiotic metabolism network model, the edges represent causal relationships between backbone nodes, as well as causal relationships between backbone nodes and each of their corresponding measurable nodes that may be reported in the literature. For example, an edge may represent a "binds to" relation, an "is expressed in" relation, an "are co-regulated based on expression profiling" relation, an "inhibits" relation, a "co-occur in a manuscript" relation, or "share structural element" relation. Generally, these types of relationships describe a relationship between a pair of nodes. Thus, it is possible to represent relationships between relationships, or relationships between a relationship and another type of biological entity represented in the graph. For example a relationship between two nodes that represent chemicals may represent a reaction. This reaction may be a node in a relationship between the reaction and a chemical that inhibits the reaction. The biological activities and relationships (i.e., the nodes and edges) that make up the network model may be stored as a web of interrelated nodes in a database. In some embodiments, the network model includes non-causal edges, which connect different forms of the biological entity.

In the present disclosure, xenobiotic metabolism is a feature of interest of a biological system. Accordingly, the interconnecting backbone nodes of the xenobiotic metabolism network model collectively represent the biological mechanism or a part thereof that operates to metabolize xenobiotic substances in the biological system. Most of the backbone nodes are associated each with an activity value that can be inferred from the biological activity measures of the measurable nodes according to the network model. For example, the network includes a backbone node representing the concentration of aryl hydrocarbon receptor (AHR) as well as a backbone node representing the transcriptional activity of aryl hydrocarbon receptor (taof(AHR)). In an example, the backbone node that corresponds to AHR has causal relationships with at least the seventeen measurable nodes that are listed in Table 1 as having a causal relationship with the backbone node AHR. The directionality of each of the causal relationships is also provided in Table 1. AHR regulates the expression of several genes of interest in the model (such as CYP1A1, CYP1B1, for example) and is a transcription factor that is activated by xenobiotic matters. In another example, the xenobiotic metabolism network model is a computational causal network model that is represented by data that includes, consists essentially of, or consists of the BEL statements shown in Table 2. In general, other backbone nodes may represent the biological activity of other biological entities that are operative in xenobiotic metabolism, including the exposure of the tissue to a specific xenobiotic.

Figure 4A:
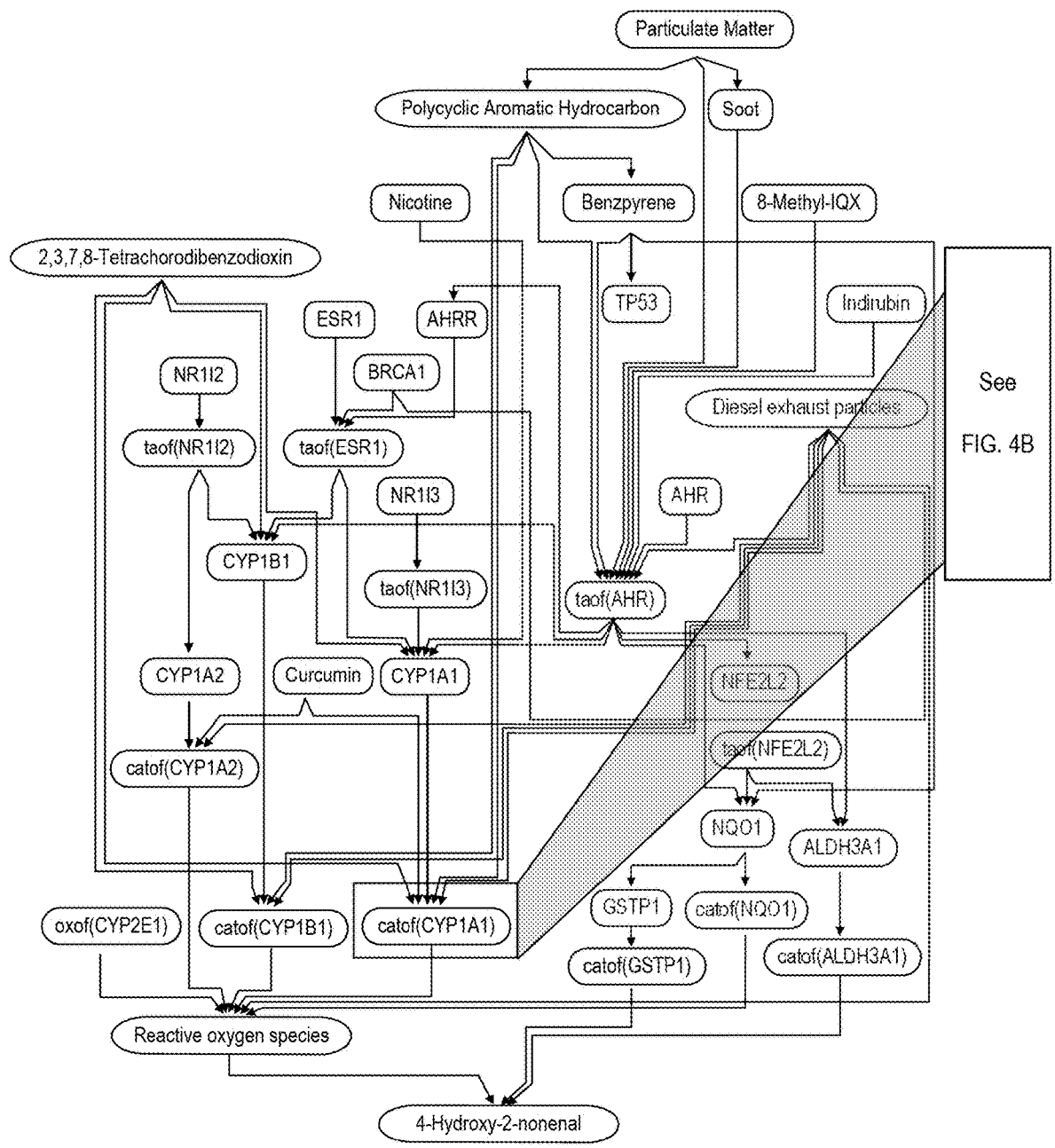
FIGS. 4A and 4B depict a xenobiotic metabolism network model.

In an example, the xenobiotic metabolism network model that can be used in the systems and methods disclosed herein is shown in FIG. 4A. In particular, the graphical illustration in FIG. 4A includes a set of backbone nodes that represent a set of biological activities which embodies various aspects of the mechanism underlying xenobiotic metabolism. The backbone nodes are connected by causal edges that carry directional information. The network model may be used to gain insight into perturbations caused by a given stimulus that relates to xenobiotic metabolism.

The xenobiotic metabolism network model provided herein was constructed from information obtained from two sources, a literature source supplying descriptions of the relevant mechanisms involved in response to xenobiotic substances, and a data set-derived source which include results of computational analysis of publicly available transcriptomic data obtained from experiments performed in pulmonary cells. In order to ensure that the network model represents biological activities related to the responses to xenobiotic substances in non-diseased or healthy pulmonary tissues of human or rodent origin, a set of rules for selecting network model content was adopted. The overall goal was to generate a network model that reflects acute, non-pathological responses, and does not include adjacent biological processes such as cell death/apoptosis, tissue damage, or inflammation. Relationships derived from human tissue context were prioritized, however, connections derived from mouse and rat were also used to complete the model. Canonical mechanisms representing pathways well-established in the literature were included in the network model even when explicit support in literature for the operation of the mechanism in lung- or cardiovascular-related tissues was not identified. The use of causal relationships with tissue contexts from immortalized cell lines was limited only to building critical mechanisms in the network model, when the only available data are derived from this type of experimental system.

The xenobiotic metabolism network model as described herein does not necessarily rely on forward assumptions (i.e., from a backbone node to a measurable node). Rather, the model may infer the activity of a backbone node based on the expression of genes (i.e., at one or more measurable nodes) that the backbone node is observed to regulate. "Forward reasoning" assumes that gene expression correlates with changes in protein activity, whereas "backward reasoning" or reverse causal reasoning (RCR) considers the changes in gene expression as the consequence of the activity of an upstream entity. By applying this reasoning technique, a xenobiotic metabolism network model is created to simulate activities at the nodes and causal relationships between the nodes. Accordingly, differential expressions of genes are experimental evidence for the activation of an upstream entity represented by a backbone node, and RCR provides insight into the biological mechanisms that give rise to the observed gene expression levels.

In an example, the xenobiotic metabolism network model may be constructed by applying RCR to identify one or more mechanisms that are likely causes of the measured quantities, such as differential gene expression levels. A mechanism that is identified by RCR may refer to a biological activity level of a backbone node that gives rise to differential gene expression levels that are observed in the measurable nodes that are connected to the backbone node. In other words, RCR identifies mechanisms that link a backbone node to a number of connected measurable nodes, which are representative of measurable quantities that the backbone node may influence or regulate. In particular, RCR can be used to process a network of the above-described causal relationships to formulate hypotheses regarding the mechanisms. In general, this set of mechanisms represent upstream regulators of downstream activities (such as downstream gene expression), the measurements of which and their differences under various experimental conditions can be ranked by statistics that evaluate relevance and accuracy, and can be used to make predictions. For example, if the abundance of an entity represented by an upstream node increases, the downstream nodes linked by causal increase relationships may be inferred to increase, and the downstream nodes linked by causal decrease relationships may be inferred to decrease.

Then, RCR evaluates the identified mechanisms against datasets of differential measurements. The causal relationships of a mechanism that link the upstream biological entity (i.e., backbone node) to downstream gene expression levels (i.e., measurable nodes) are in the form of a computable causal network model and may be used to quantify changes to a network according to network scoring methods. In some embodiments, the RCR computation applies one or more constraints for generation of a network model. Examples of constraints include but are not limited to a path length (i.e., the maximum number of edges connecting upstream nodes and downstream nodes), and possible causal paths that connect the upstream nodes to downstream nodes.

Using RCR to construct a causal network model has several advantages. First, nodes in the network are connected by causally related edges with fixed topology, allowing the biological intent of the network model to be easily understood by a scientist or a user, enabling inference and computation on the network as a whole. Second, unlike other approaches for building pathway or connectivity maps where connections are often represented out of a tissue or disease context, the network models herein are created according to appropriate tissue/cell contexts and biological processes. Third, the causal network models may capture changes in a wide range of biological molecules including proteins, DNA variants, coding and non-coding RNA, and other entities, such as phenotypic, chemicals, lipids, methylation states or other modifications (e.g., phosphorylation), as well as clinical and physiological observations. For example, a network model may be representative of knowledge from molecular, cellular, and organ levels up to an entire organism. Fourth, the network models are evolving and may be easily modified to represent specific species and/or tissue contexts by the application of appropriate boundaries and updated as additional knowledge becomes available. Fifth, the network models are transparent; the edges (cause and effect relationships) in the network model are all supported by published scientific findings anchoring each network to the scientific literature for the biological process being modeled.

In some embodiments, the xenobiotic metabolism network model is encoded in a structured language that represents technical findings by capturing causal and correlative relationships between biological entities. The language enables the formation of computable statements that are composed by functions and entity definitions expressed with a defined ontology (e.g. HGNC). Biological Expression Language™ (BEL™) is an example of such a language used in an implementation of the present disclosure and is a syntax for recording the inter-relationships between biological entities. A BEL statement is a semantic triple (subject, predicate, object) that represents a discrete scientific causal relationship and its relevant contextual information.

In an example, the xenobiotic metabolism network model may be provided as a set of BEL statements which describe the relationships between backbone nodes, as well as relationships between backbone nodes and measurable nodes. Table 1 includes a set of five exemplary backbone nodes (left column) and their downstream connections to corresponding measurable nodes (middle column). As shown in Table 1, genes are listed in accordance with their standard gene symbols, some or all of which have been approved by the Human Genome Organisation Gene Nomenclature Committee. The relationship value (right column) indicates whether the relationship between the backbone node and the measurable node is a causal increase relationship (+1) or a causal decrease relationship (−1). In a causal increase relationship, if an amount of biological activity at the backbone node increases, the amount of biological activity at the downstream measurable node increases. In a causal decrease relationship, if an amount of biological activity at the backbone node increases, the amount of biological activity at the downstream measurable node decreases. All these relationships between a backbone node and a measurable node can be encoded in BEL.

Table 2 includes a list of 64 BEL statements that represent a set of interconnected backbone nodes. In particular, the left column of Table 2 indicates a source node, the right column of Table 2 indicates a target node, and the middle column indicates the relationships between the corresponding source nodes and target nodes. The symbols for the relationships listed in the middle column of Table 2 correspond to symbols recognized by the BEL community, which are listed on the BEL website. For example, the symbols represent causal relationships or relationships between the corresponding symbol nodes and target nodes. In particular, the symbol "→" indicates an increasing causal relationship, the symbol "=>" indicates a directly increasing causal relationship, the symbol "−1" indicates a decreasing causal relationship, and the symbol "=1" indicates a directly decreasing causal relationship. Furthermore, the symbol "−sub→" indicates that the target node is a subset or a portion of the source node, the symbol "–cat→" indicates that the target node represents the catalytic activity of the source node, and the symbol "–e→" indicates that the target node represents the transcriptional activity of the source node. The meanings of these symbols are also summarized in the legend that follows Table 2.

While the xenobiotic metabolism model described by the BEL statements in Table 2 is adequate for use in the methods provided by the present disclosure, it is contemplated that one of skill in the art can supplement the model by including additional backbone nodes based on RCR and relevant literature or data sets. Accordingly, the methods disclosed herein involve a xenobiotic metabolism network model that can be described by a set of BEL statements comprising, consisting essentially of, or consisting of the BEL statements in Table 2. In various implementations, only a substantial number of the BEL statements in Table 2 which connect the most important backbone nodes are required. The relative importance of each of the backbone nodes to the network model can be estimated by the individual score of each backbone nodes. See for example in FIG. 6B, the individual scores of the backbone nodes are indicated by different shadings, ranging from −0.02 to 0.16. As is described in detail below, the values of the scores for the backbone nodes indicate a perturbation of a tissue caused by an agent, and may be network perturbation amplitude scores (NPA scores), scores provided by ingenuity pathway analysis (IPA), or scores provided by gene set enrichment analysis (GSEA).

In the model, for each of the backbone nodes (source nodes and target nodes) shown in Table 2, there is a corresponding set of measurable node(s) that can be used to infer the activities of a backbone node. One of skill in the art can readily identify the measureable nodes corresponding to a backbone node based on RCR and relevant literature or data sets. As shown in Table 1, one or more measurable nodes may be used to infer the activities of each of the five backbone nodes. However, in various embodiments, measurements of biological activities of all the measurable nodes that are listed as connected to a backbone node are not necessary to infer a biological activity value of the backbone node. Measurements from a subset of the connected measurable nodes may be enough to properly infer the activity of a backbone node. Alternatively, one of skill in the art may supplement the sets of measurable nodes by searching literature databases to identify additional genes, the expressions of which are causally related to the one or more backbone nodes listed in Table 2, in the context of xenobiotic metabolism.

Various methods of obtaining gene expression level measurements from a tissue may be used, including in vitro and in vivo measurements. Example methods for obtaining measurements from tissue cultures and the corresponding data are shown and described in relation to FIGS. 5-8, in the section entitled "Example Correlations Studies for Exposure to Cigarette Smoke." However, the examples described herein are for illustrative purposes only, and one of skill in the art will understand that in general, the systems and methods described herein may be used to apply to data obtained using other methods, without departing from the scope of the present disclosure.

A biological system in the context of the present disclosure is an organism or a part of an organism, including functional parts, the organism being referred to herein as a subject. Generally, the target biological tissues or surrogate biological tissues, derived from a subject are used or investigated in the methods of the present disclosure. The subject is generally a mammal, including a human. The subject can be an individual human being in a human population. The term "mammal" as used herein includes but is not limited to a human, non-human primate, mouse, rat, dog, cat, cow, sheep, horse, pig, and rodents. Mammals other than humans can be advantageously used as subjects that can be used to provide a model of a human disease. The non-human subject can be unmodified, or a genetically modified animal (e.g., a transgenic animal, or an animal carrying one or more genetic mutation(s), or silenced gene(s)). A subject can be male or female. Depending on the objective of the operation, a subject can be one that has been exposed to an agent of interest. A subject can be one that has been exposed to an agent over an extended period of time, optionally including time prior to the study. A subject can be one that had been exposed to an agent for a period of time but is no longer in contact with the agent. A subject can be one that has been diagnosed or identified as having a disease. A subject can be one that has already undergone, or is undergoing treatment of a disease or adverse health condition. A subject can also be one that exhibits one or more symptoms or risk factors for a specific health condition or disease. A subject can be one that is predisposed to a disease, and may be either symptomatic or asymptomatic. In certain implementations, the disease or health condition in question is associated with exposure to an agent or use of an agent over an extended period of time.

Depending on the context of the operation, the biological system can be defined at different levels as it relates to the function of an individual organism in a population, an organism generally, an organ, a tissue, a cell type, an organelle, a cellular component, or a specific individual's cell(s). Each biological system comprises one or more biological mechanisms or pathways, the operation of which manifest as functional features of the system. Animal systems that reproduce defined features of a human health condition and that are suitable for exposure to an agent of interest are preferred biological systems. Cellular and organotypic systems that reflect the cell types and tissue involved in a disease etiology or pathology are also preferred biological systems. The biological system contemplated for use with the systems and methods described herein can be defined by, without limitation, functional features (biological functions, physiological functions, or cellular functions), organelle, cell type, tissue type, organ, development stage, or a combination of the foregoing. Examples of biological systems include, but are not limited to, the pulmonary (e.g., pulmonary inflammation), integument, skeletal, muscular, nervous (central and peripheral), endocrine, cardiovascular, immune, circulatory, respiratory, urinary, renal, gastrointestinal, colorectal, hepatic and reproductive systems. Other examples of biological systems include, but are not limited to, the various cellular functions in epithelial cells, nerve cells, blood cells, connective tissue cells, smooth muscle cells, skeletal muscle cells, fat cells, ovum cells, sperm cells, stem cells, lung cells, brain cells, cardiac cells, laryngeal cells, pharyngeal cells, esophageal cells, stomach cells, kidney cells, liver cells, breast cells, prostate cells, pancreatic cells, islet cells, testes cells, bladder cells, cervical cells, uterus cells, colon cells, and rectum cells. Some of the cells may be cells of cell lines, cultured in vitro or maintained in vitro indefinitely under appropriate culture conditions. Examples of cellular functions include, but are not limited to, cell proliferation (e.g., cell division), degeneration, regeneration, senescence, control of cellular activity by the nucleus, cell-to-cell signaling, cell differentiation, cell de-differentiation, cell stress response, xenobiotic metabolism, autophagy, necroptosis, secretion, migration, phagocytosis, repair, apoptosis, and developmental programming Examples of cellular components that can be considered as biological systems include, but are not limited to, the cytoplasm, cytoskeleton, membrane, ribosomes, mitochondria, nucleus, endoplasmic reticulum (ER), Golgi apparatus, lysosomes, DNA (e.g., DNA damage or DNA repair), RNA, proteins, peptides, and antibodies.

A "sample" as used herein refers to any matter that is isolated from a subject or an experimental system (e.g., cell, tissue, organ, or whole animal). A sample can include, without limitation, a single cell or multiple cells, cellular fraction, tissue biopsy, resected tissue, tissue extract, tissue, tissue culture extract, tissue culture medium, exhaled gases, whole blood, platelets, serum, plasma, erythrocytes, leucocytes, lymphocytes, neutrophils, macrophages, B cells or a subset thereof, T cells or a subset thereof, a subset of hematopoietic cells, endothelial cells, synovial fluid, lymphatic fluid, ascites fluid, interstitial fluid, bone marrow, cerebrospinal fluid, pleural effusions, tumor infiltrates, saliva, mucous, sputum, semen, sweat, urine, or any other bodily fluids. Samples can be obtained from a subject by means including but not limited to venipuncture, excretion, biopsy, needle aspirate, lavage, scraping, surgical resection, or other means known in the art.

The sample is used to obtain biological activity measures including differential gene expression levels of a set of genes. The differential gene expression levels may be obtained from a set of contrast data that is representative of a difference between treatment data and control data. The treatment data corresponds to a response of the sample to an agent, while the control data correspond to the response of the same sample under control conditions, for example, the absence of the agent.

Xenobiotic metabolism is one of the primary responses when a biological system is exposed to a substance that is foreign to it. Therefore, any increase in xenobiotic metabolism may indicate an exposure to a xenobiotic substance. Changes in xenobiotic metabolism may further indicate the development of adverse effects in the exposed biological system, diseases and even cancers. The computational systems and methods described herein assess objectively and quantitatively the magnitude of changes within a biological system when it is perturbed by an agent. In particular, the magnitude of changes can be represented by a "score," which is a value or a set of values that provide a quantitative measure of the magnitude of changes in a biological system.

In one aspect, a score that reflects changes in xenobiotic metabolism can be used to detect the exposure of a biological system to a xenobiotic substance. In another aspect, a score that reflects changes in xenobiotic metabolism can be used to estimate the overall biological effect caused by the exposure of the biological system to a xenobiotic substance. In various embodiments, the score can be used to assess and compare changes in the biological system caused by exposure to manufactured products (for safety assessment or comparisons), therapeutic compounds including nutrition supplements (for determination of efficacy or health benefits), and environmentally active substances (for prediction of risks of long term exposure and the relationship to adverse effect and onset of disease), among others. The score may also be used to predict whether a patient will be responsive to a drug or the magnitude of any adverse reactions due to use of the drug. The scores obtained for different agents can be used to compare the relative impact of the different agents on the biological system.

Various supervised methods of analysis which use predetermined aggregations of genes (or gene sets) rather than individual genes to assess for coordinate expression within samples or sample classifications are known in the art and may be applied. The computation of the score uses as input, a set of gene expression data obtained from a controlled experiment or clinical trial in which a biological system is perturbed by an agent. The xenobiotic metabolism network model comprises a set of measurable nodes which corresponds to a predetermined set of genes, the expression levels of which are measured and the data collected. The expression levels of genes in this predetermined set collected from cells which were exposed to an agent are referred to herein as treatment data. Gene expression levels of the same genes collected from cells which were not exposed to the agent or which were exposed under different conditions, are referred to as control data. The difference between the treatment data and the control data for each measurable node is the activity measure for that measurable node. In some implementations, the activity measure is expressed in terms of fold-change which is a numerical value describing the magnitude of change between control data and treatment data, or between two sets of data representing different treatment conditions. The activity measure for each node may include a logarithm of the difference between the treatment data and the control data.

In some embodiments, the score generated by the systems and methods of the invention is a network perturbation amplitude (NPA) score described in patent publication WO2013/034300 and PCT Application Nos. PCT/EP2013/062979 and PCT/EP2012/061035, each of which is incorporated herein by reference in its entirety. A NPA score may be computed by translating measurements of biological activities at the measurable nodes into activity values of the backbone nodes using a difference statement that represents the difference between the activity measure of a measurable node and the activity measure of the backbone node to which it is connected via an edge. In some implementations, the following difference statement may be used:

$$\sum_{x \to y} (f(x) - \text{sign}(x \to y) f(y))^2 w(x \to y) \qquad (6)$$

where f(x) denotes an activity value (for nodes x in the second set of nodes) or measure (for nodes x in the first set of nodes), sign(x→y) denotes the direction value of the edge in the xenobiotic metabolism network model that connects the node representing biological entity x to the node representing biological entity y, and w(x→y) denotes a weight associated with the edge connecting the nodes representing entities x and y. The activity values of the backbone nodes can be generated by performing an optimization in accordance with a difference objective. The difference objective may specify that the difference statement is to be maximized, minimized, or made as close as possible to a target value. For the optimization, the smoothest function (accounting for the sign of the causal edges in the network model) can be derived by imposing a boundary condition on the backbone nodes corresponding to the measurements. This difference objective may be written as the following computational optimization problem:

$$\text{argmin}_{f \in \mathcal{F}(V)} \Sigma_{x \to y} (f(x) - \text{sign}(x \to y) f(y))^2 \cdot w(x \to y) \text{ such that } f|_{V_0} = \beta, \qquad (8)$$

where β represents the activity measure for each of the measurable nodes. To address the difference objective, the xenobiotic metabolism network model is computationally characterized, for example, via a weighted or non-weighted adjacency matrix. In an example, given the difference objective is formulated according to Eq. 8, above, the xenobiotic metabolism network model is characterized using a signed Laplacian matrix defined in accordance with $$L = \mathrm{diag(out)} + \mathrm{diag(in)} - (A + A^T). \quad (9)$$

Given this characterization, the difference objective of Eq. 8 can be represented as $$\mathrm{argmin}_{f \in l^2(V)} f^T L f \text{ such that } f|_{V_0} = \beta.$$

In some implementations, the NPA score may be calculated in accordance with:

$$NPA(G, \beta) = \qquad (1)$$
$$\frac{1}{|\{x \to y\} \text{ s.t. } x, y \notin V_0|} \sum_{\substack{x \to y \\ s.t. \ x,y \notin V_0}} (f(x) + \mathrm{sign}(x \to y) f(y))^2,$$

where $V_0$ denotes the measurable nodes (i.e., those for which treatment and control data are received), f(x) denotes the activity value generated for the biological entity x, and sign(x→y) denotes the direction value of the edge in the computational network model that connects the node representing biological entity x to the node representing biological entity y. If the vector of activity values associated with the backbone nodes is denoted f2, the NPA score may be commuted via the quadratic form:

$$NPA = f_2^T Q f_2, \quad (2)$$

where $$Q = \frac{1}{|\{x \to y\} \text{ s.t. } x, y \notin V_0|} \left[ \left( \mathrm{diag}(\mathrm{out} \, |_{l^2(V \setminus V_0)}) + \mathrm{diag}(\mathrm{in} \, |_{l^2(V \setminus V_0)}) - (-A - A^T) \right) |_{l^2(V \setminus V_0)} \right] \in l^2(V \setminus V_0) \quad (3)$$

and where diag(out) denotes the diagonal matrix with the out-degree of each node in backbone nodes, diag(in) denotes the diagonal matrix with the in-degree of each node in the backbone nodes, and A denotes the adjacency matrix of the xenobiotic metabolism network model limited to only those backbone nodes and defined in accordance with $$A_{xy} = \begin{cases} \mathrm{sign}(x \to y) & \text{if } x \to y \\ 0 & \text{else} \end{cases}. \quad (4)$$

If A is a weighted adjacency matrix, then element (x,y) of A may be multiplied by a weight factor w(x→y). In certain implementations, the NPA score is computed as a (semi-) Sobolev-type norm on a signed directed graph underlying the xenobiotic metabolism network model which can be expressed as a quadratic form.

Figure 6A:
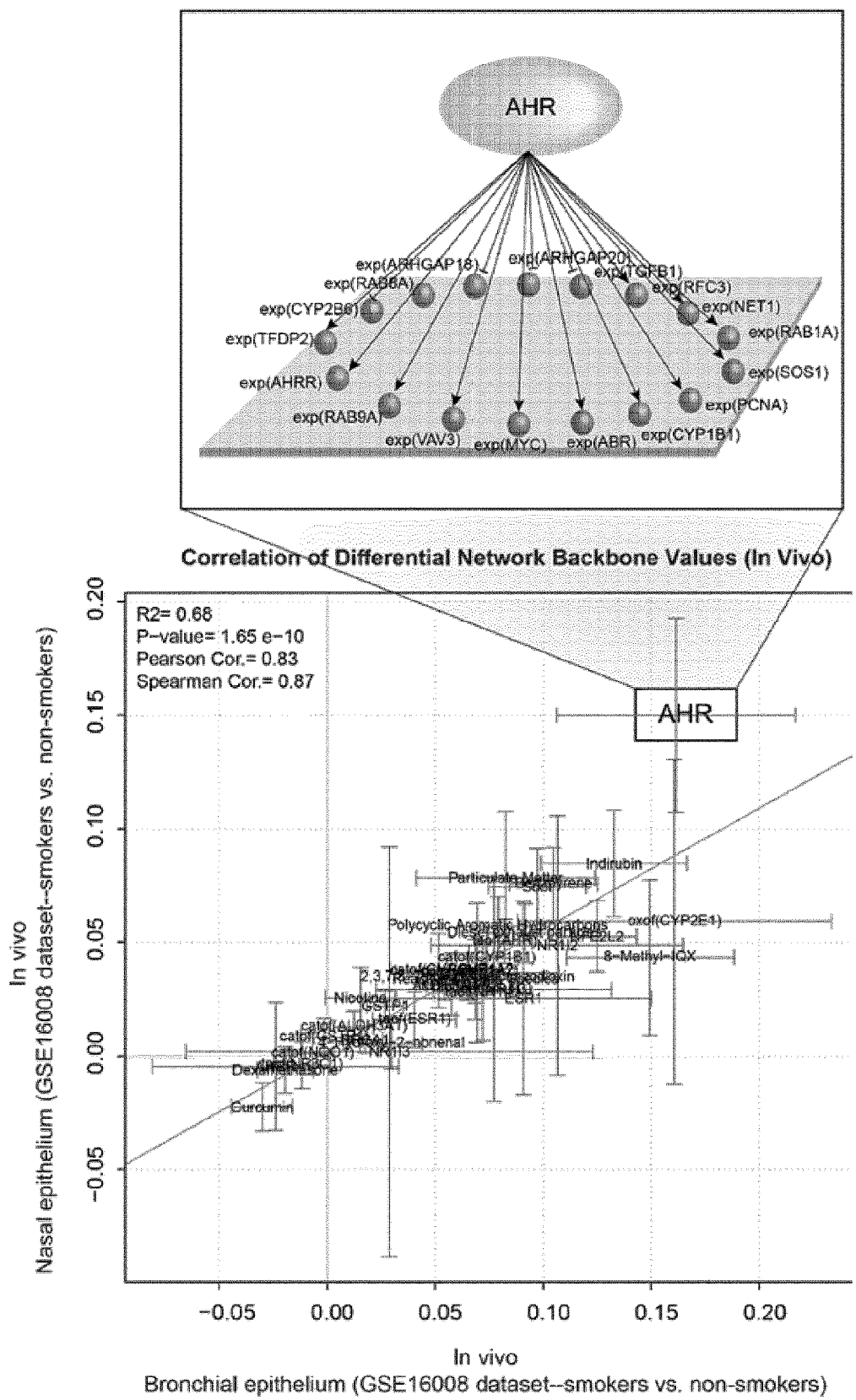
FIG. 6A depicts activity values of backbone nodes for in vivo bronchial and nasal brushing data.
Figure 6B:
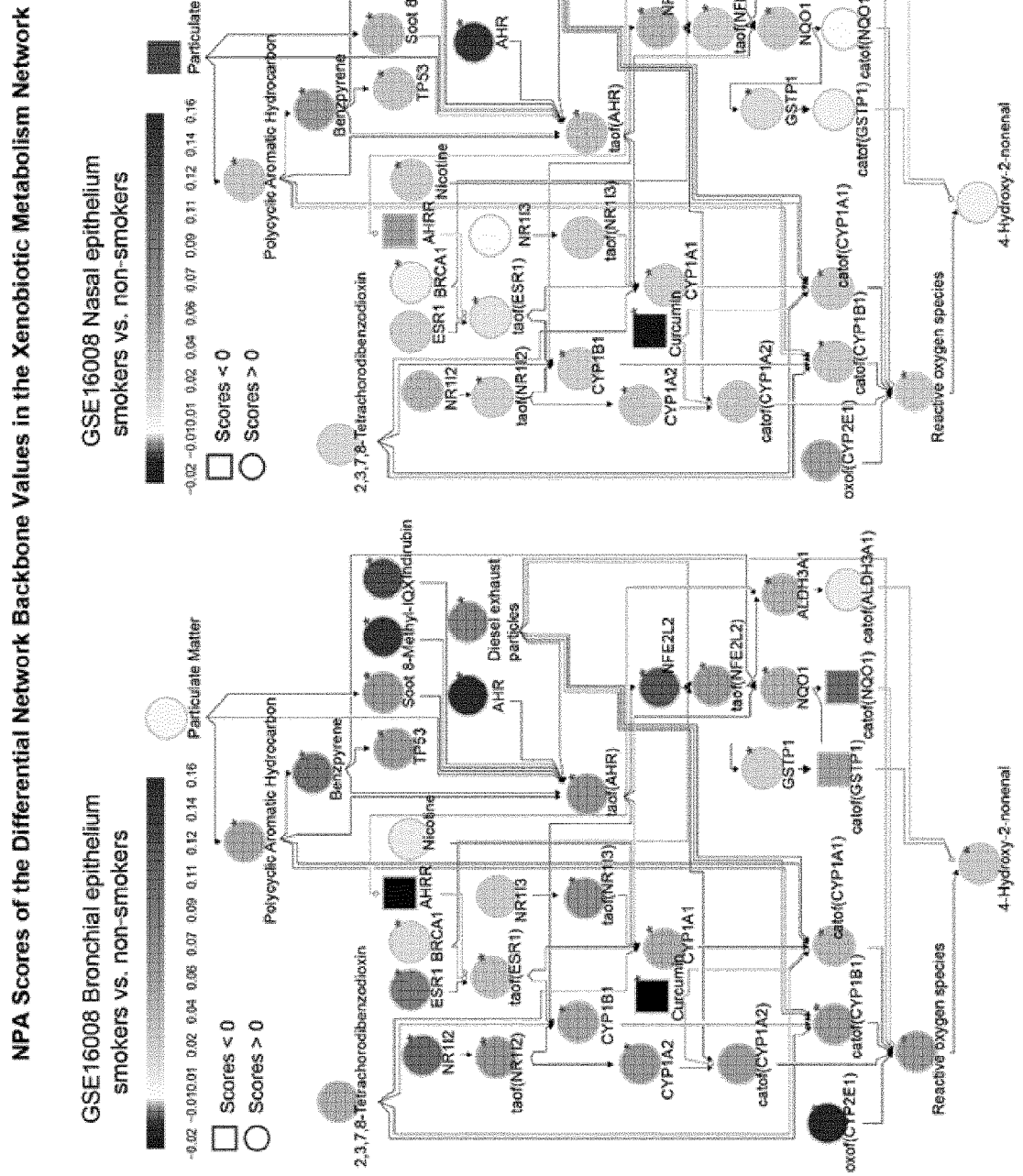
FIG. 6B depicts activity values of backbone nodes using in vivo bronchial and nasal data.
Figure 6C:
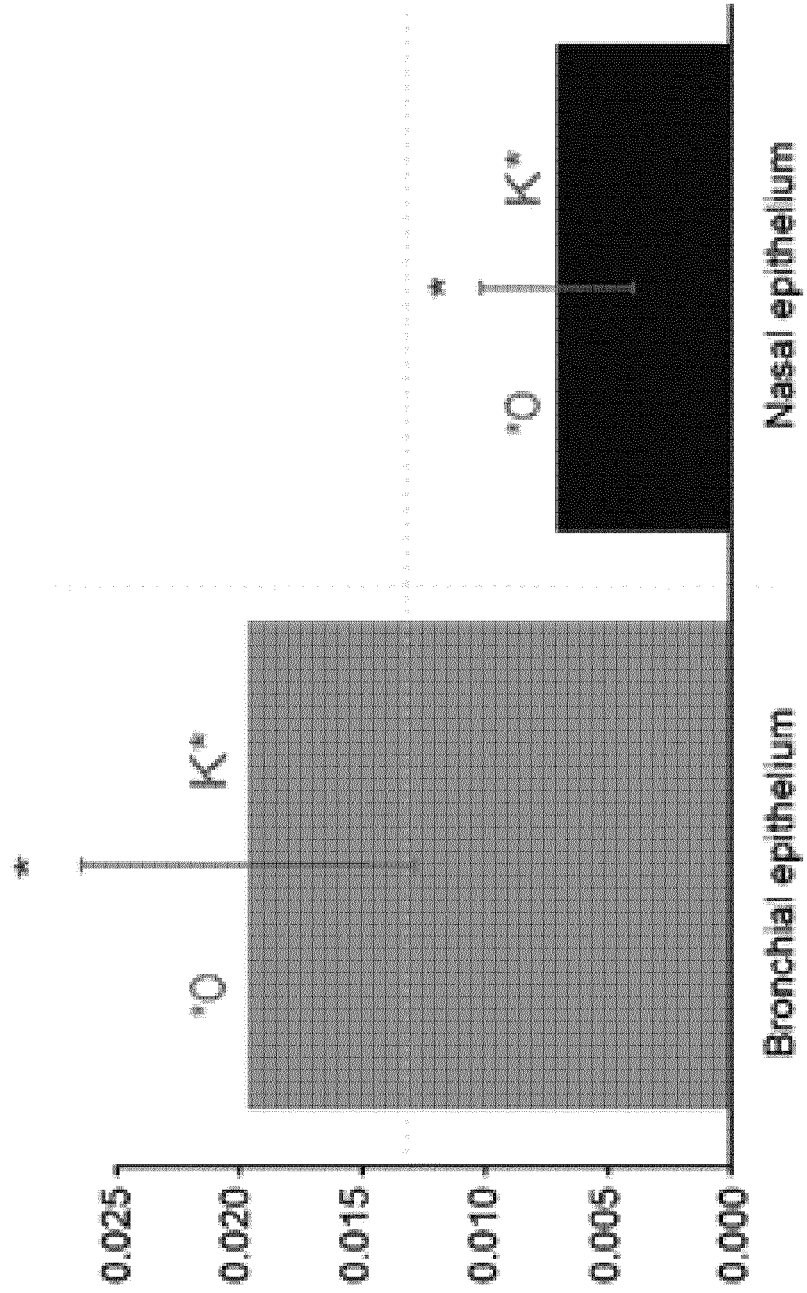
FIG. 6C depicts network perturbation amplitude scores for bronchial and nasal samples.

FIGS. 6B and 6C are described in detail below, but briefly, FIG. 6B is a graphical illustration of the activity values of backbone nodes in a xenobiotic metabolism network model using in vivo bronchial (left) and nasal (right) data, and FIG. 6C shows bar plots of the corresponding NPA scores for the xenobiotic metabolism network model. In FIG. 6B, the different shades of the backbone nodes reflect the quantification of the backbone nodes derived from the NPA scoring technique that demonstrates the biological mechanisms pertaining to xenobiotic metabolism. Negative values indicate downregulation of the backbone node activity, and positive values indicate upregulation of the backbone node activity. As is explained in detail below, the NPA scores shown in FIG. 6C are statistically significant, suggesting that both in vivo nasal and bronchial samples significantly demonstrate the biological mechanisms represented in the xenobiotic metabolism network model.

Figure 4B:
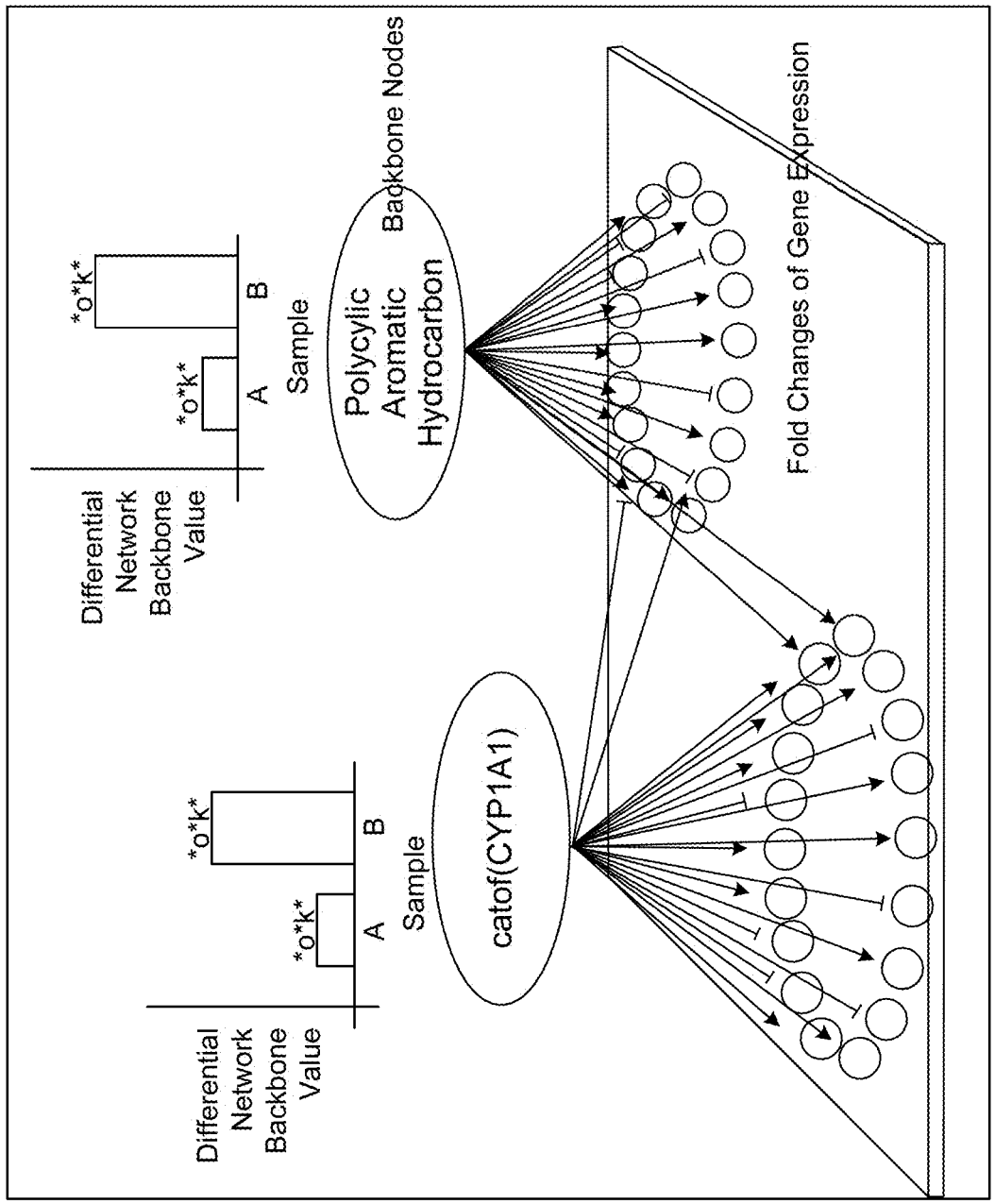

In another example, FIG. 4B shows a graphical illustration of the causal relationships between two example backbone nodes and the connected measurable nodes. The activities of the backbone nodes (ovals) characterize functional aspects of the network model constituting a functional layer, and the gene expression levels of the measurable nodes (circles) constitute a second layer of nodes (transcriptional layer) in the network model characterized by transcriptional activities of genes corresponding to the measurable nodes. The expression of a given gene (a measurable node) may be modulated by one or more backbone nodes as depicted by the arrows (with arrowheads for causal increase relationships and dashes for causal decrease relationships). In forward reasoning, the measured gene expression levels are assumed to be direct surrogates for their associated proteins or protein functions. In contrast, a backward reasoning approach scores the biological processes represented by the functional layer (backbone nodes) based on the gene expression levels at the transcriptional layer (measurable nodes). In this way, the quantification of the backbone nodes reflects the biological mechanisms related to xenobiotic metabolism.

In some embodiments, confidence intervals are computed in relation to the NPA score. The confidence intervals may account for experimental error (e.g., the biological variation between samples in an experimental group). Furthermore, companion statistics may be computed to quantify the specificity of the resulting NPA score to the mechanisms described in the xenobiotic metabolism network model. In particular, as the NPA score is represented by a quadratic function of the measurements at the measurable nodes, the statistical variance of an NPA score may be computed from the variances of the measurements. Then, the central limit theorem may be used to derive a confidence interval.

In some embodiments, one or both of two permutation tests are implemented. A first permutation test assesses an importance of a position of the measurable nodes within the network to the measured values. In this case, the gene labels of the measurable nodes are reshuffled, NPA scores are re-computed for each reshuffling, and a permutation P-value is derived (denoted by *O in FIG. 4B when the value is <0.05). The first permutation test thus assesses whether the resulting NPA scores were specific to the underlying evidence (i.e., gene expression levels of the measurable nodes) in the xenobiotic metabolism network model. A second permutation test assesses whether the functional layer (backbone nodes) network significantly contributed to the amplitude of the network perturbation (denoted by K* in the figures when the value is <0.05). The network may be considered to be specifically perturbed if both P-values from the two permutation tests are low (typically <0.05), and if the perturbation was significant when the confidence interval was greater than 0. A P-value that is small, for example less than 0.5%, less than 1%, less than 5%, or any other fraction, indicates that a proposed NPA score is statistically significant. The methods for computing a NPA score as disclosed herein may include one or both of these permutation tests to supply the respective statistics.

In some embodiments, another scoring method can be applied to generate, for example an Ingenuity® Pathway Analysis (IPA) score. As used herein, the IPA score represents a fit of the xenobiotic metabolism network model to a set of measurements (which may be a user-defined set of genes referred to as Focus Genes). The IPA score is derived from a statistical p-value and indicates the likelihood of the Focus Genes being together in a network due to random chance. An Ingenuity® Knowledge Base (IKB) may be used to determine the IPA score by first generating the xenobiotic metabolism network model. The IKB includes an aggregation of results determined from a set of publications, such that each causal connection and each node in the xenobiotic metabolism network model is supported by evidence extracted from the publications.

Methods for computing an IPA score are known in the art and software packages for computing an IPA score are commercially available (Ingenuity Systems, Redwood City, US). The generation of a network using the IPA process may include sorting the Focus Genes with respect to their interconnectivity. In an example, highly interconnected Focus Genes may be processed before other Focus Genes that are less connected. Then, small network portions are constructed from the Focus Genes, and the small network portions are merged using "linker" genes, which provide connections across the small network portions. In particular, the linker genes may be those that have the most edges in multiple small network portions. Then, for network portions that are still small (i.e., those that have fewer than 35 (or any other suitable number) genes, for example), other genes may be provided to the periphery of the small network portion to provide additional biological context to the Focus Genes. Finally, a p-score may be computed from hypergeometric p-values using a significance test such as Fisher's exact test. In particular, the p-value may correspond to the right-tailed sum of the hypergeometric distribution, and the p-score may be computed as p score=$-\log_{10}$(p value).

In some embodiments, the score can be generated by another technique well known in art, referred to as gene set enrichment analysis (GSEA), which evaluates microarray data at the level of gene sets. [Subramanian A, Tamayo P, Mootha V K, Mukherjee S, Ebert B L, Gillette M A, Paulovich A, Pomeroy S L, Golub T R, Lander E S, Mesirov J P: Gene set enrichment analysis: A knowledge-based approach for interpreting genome-wide expression profiles. Proc. Natl. Acad. Sci. 2005, 102(43):15545-50.] In GSEA, genes are ranked based on a correlation between the gene expression levels and the class distinction. This analysis is performed by (i) ranking all genes in the data set based on their correlation to a chosen phenotype, (ii) identifying the rank positions of all members of the gene set, and (iii) calculating an enrichment score (ES) that represents the difference between the observed rankings and that which would be expected assuming a random rank distribution. After establishing the ES for each gene set across the phenotype, GSEA reiteratively randomizes the sample labels and retests for enrichment across the random classes. By performing repeated class label randomizations, the ES for each gene set across the true classes can be compared to the ES distribution from the random classes. Those gene sets that significantly outperform iterative random class permutations are considered significant. The score may reflect the degree to which a gene set is overrepresented at the top or bottom of a ranked list and may correspond to a weighted Kolmogorov Smirnov-like statistic.

In some embodiments, another method known in the art may be used to generate a score, known as a strength score, as described in U.S. Pat. No. 8,417,661, which is incorporated herein by reference in its entirety. In an example, the strength score is measured as a weighted average of adjusted log-fold changes or differential expression levels for a set of measurable nodes. In particular, the strength score may be an amplitude value that corresponds to a difference between two weighted sums. One sum is of the log 2 of the differential expression levels of the measurable nodes that are expected to increase (those with causal increase (or decrease) relationships with respect to a particular backbone node, for example), and the other sum is the log 2 of the differential expression levels of the measurable nodes that are expected to decrease (those with causal decrease (or increase) relationships with respect to a particular backbone node, for example). In this way, the log-fold changes are "adjusted" by accounting differently for those nodes that are expected to increase and those that are expected to decrease. The difference may be divided by a number of measurable nodes to obtain the strength score as a normalized value of change for each node. The weights applied to the measurable nodes may be the same (a unitary weight of value 1, for example) or different. In some embodiments, the strength score is used to predict an activity level at a reference node. For example, when the strength score is positive, a reference node may be predicted to increase, while the reference node may be predicted to decrease for a negative strength score.

The computational systems and methods described herein also identify correlations of scores between a pair of biological tissues. In particular, one biological tissue may be referred to as a "target biological tissue," and the other biological tissue may be referred to as a "surrogate biological tissue." In some cases, it is difficult for a user to obtain a sample from a target biological tissue. However, the user may have data or measurements of a sample of a surrogate biological tissue, which may be correlated with the hypothetical measurements of the target biological tissue and which are easier for the user to access. The difficulty in obtaining the target biological tissue may arise for any number of reasons. For example, collecting data from the desired target biological tissue may require recording in vivo data from the tissue, which may be very invasive technique and may not be acceptable or possible experimentally. However, if the user has access to an organotypic culture of the tissue, in vitro data may be obtained under less challenging conditions and the in vitro data may present a more economical solution. The use of organotypic culture may reduce the use of live animals in product testing, toxicology testing, drug development research. In another example, bronchial or lung tissue may be more difficult to access than nasal tissue, and nasal tissue may serve as the surrogate biological tissue for the target bronchial or lung tissue.

The correlation between a sample of a target biological tissue and a sample of a surrogate biological tissue may be determined from previously performed correlation experiments. Specific examples of correlation experiments are described in detail in relation to FIGS. 5-8 and Tables 3 and 4. For example, actual samples of the target biological tissue and the surrogate biological tissue may have previously been obtained, and gene expression levels may have been measured from the samples that were exposed to an agent (i.e., treatment data) and from the samples that were not exposed to the agent (i.e., control data). The measurements may be provided as inputs to the computational causal network model, which may set activity measures of the measurable nodes to values derived from the measurements. Then, biological activity values for at least some of the backbone nodes may be obtained for each of the samples. In particular, a first set of biological activity values for the backbone nodes is obtained for the actual target biological sample, and a second set of biological activity values for the backbone nodes is obtained for the actual surrogate biological sample. The correlation may be determined by identifying a correlation between the first and second sets of biological activity values for corresponding backbone nodes. For example, Pearson correlation coefficients and Spearman correlation coefficients are shown in Tables 3 and 4 for various combinations of target and surrogate biological samples, though one of skill in the art will understand that any other suitable type of correlation coefficient may be used in accordance with the systems and methods described herein to represent a correlation between target and surrogate biological samples. In another example, a score representative of an amount of perturbation to the biological sample may be assessed based on the biological activity values, and the score for the sample of the target biological tissue may be correlated with the score for the sample of the surrogate biological tissue.

In any case, the correlation experiments may have been previously performed and published, such that a user is aware of a correlation and makes use of the correlation to use the surrogate biological tissue as a proxy for the target biological tissue, which may be more difficult or just uneconomic to obtain. Thus, upon identifying the correlation, the user provides data recorded from a sample of the surrogate biological tissue to the computational causal network model, which provides activity values of the backbone nodes. The user may then use the correlation to infer that the provided activity values for the surrogate biological tissue are similar or correlated with the hypothetical activity values that would result for the target biological tissue. Similarly, a score representative of a perturbation of the network model for the sample of the surrogate biological tissue may be inferred to be similar or correlated with the hypothetical perturbation of the network model for a sample of the target biological tissue. By providing a way for a user to identify a correlation between a surrogate biological tissue and a target biological tissue, the systems and methods described herein are especially useful when it is more experimentally challenging or expensive to obtain a sample of the target biological tissue compared to a sample of the surrogate biological tissue. The user may already have data or measurements from a sample of a surrogate biological tissue, or have convenient access to such data. By exploiting the correlation between the surrogate biological tissue and the target biological tissue, the user may use the measurements from the surrogate biological tissue to infer the values of hypothetical measurements from the target biological tissue.

An agent can be a single substance or a mixture of substances, including a mixture in which not all constituents are identified or characterized. The chemical and physical properties of an agent or its constituents may not be fully characterized. An agent can be defined by its structure, its constituents, or a source that under certain conditions produces the agent. An example of an agent is a xenobiotic substance, that is a molecule or an entity that is not present in or derived from the biological system, and any intermediates or metabolites produced therefrom after contacting the biological system. An agent can be a carbohydrate, protein, lipid, nucleic acid, alkaloid, vitamin, metal, heavy metal, mineral, oxygen, ion, enzyme, hormone, neurotransmitter, inorganic chemical compound, organic chemical compound, environmental agent, microorganism, particle, environmental condition, environmental force, or physical force. Non-limiting examples of agents include but are not limited to nutrients, metabolic wastes, poisons, narcotics, toxins, therapeutic compounds, stimulants, relaxants, natural products, manufactured products, dermatologics, cosmetics, food substances, pathogens (prion, virus, bacteria, fungi, protozoa), particles or entities whose dimensions are in or below the micrometer range, by-products of the foregoing and mixtures of the foregoing. Non-limiting examples of a physical agent include radiation, electromagnetic waves (including sunlight), increase or decrease in temperature, shear force, fluid pressure, electrical discharge(s) or a sequence thereof, or trauma. An agent may cause changes to the sample, depending on which part(s) of the biological system is exposed and the exposure conditions. Non-limiting examples of an agent may include a carcinogen, an irritant, an environmental pollutant, a drug, a drug candidate, any product used for nicotine replacement therapy, or an ingredient in a consumer product, food product, beverage product, or nutritional supplement.

In various embodiments, the agent that is used to contact a sample of the target or surrogate biological tissue may be an airborne pollutant that may be inhaled by a subject. In this case, the agent may include the following non-limiting examples: tobacco smoke, cigarette smoke (CS), an aerosol including nicotine, an aerosol generated by heating tobacco, an aerosol generated by heating without combusting tobacco, or any one or more isolated constituents of the foregoing, carbon monoxide, soot, exhaust caused by combusting any hydrocarbon fuel, gasoline exhaust, diesel exhaust, coke oven emissions, airborne particular matter of various size ranges, airborne compounds comprising heavy metal (cadmium, chromium, lead, manganese, mercury, nickel), antimony, or arsenic, mineral fiber emissions from facilities manufacturing or processing glass, rock, or slag fibers (or other mineral derived fibers) of average diameter 1 micrometer or less, polycyclic organic matter such as organic compounds with more than one benzene ring and which have a boiling point greater than or equal to 100° C., acetaldehyde, acetamide, acetonitrile, acetophenone, 2-acetylaminofluorene, acrolein, acrylamide, acrylic acid, acrylonitrile, allyl chloride, 4-aminobiphenyl, aniline, o-anisidine, asbestos, benzene (including benzene from gasoline), benzidine, benzotrichloride, benzyl chloride, biphenyl, bis (2-ethylhexyl)phthalate (dehp), bis(chloromethyl)ether, bromoform, 1,3-butadiene, calcium cyanamide, caprolactam, captan, carbaryl, carbon disulfide, carbon tetrachloride, carbonyl sulfide, catechol, chloramben, chlordane, chlorine, chloroacetic acid, 2-chloroacetophenone, chlorobenzene, chlorobenzilate, chloroform, chloromethyl methyl ether, chloroprene, cresols/cresylic acid (isomers and mixture), o-cresol, m-cresol, p-cresol, cumene, dichlorodiphenyldichloroethylene, diazomethane, dibenzofurans, 1,2-dibromo-3-chloropropane, dibutylphthalate, 1,4-dichlorobenzene(p), 3,3-dichlorobenzidene, dichloroethyl ether (bis(2-chloroethyl)ether), 1,3-dichloropropene, dichlorvos, diethanolamine, n,n-dimethylaniline, diethyl sulfate, 3,3-dimethoxybenzidine, dimethyl aminoazobenzene, 3,3'-dimethyl benzidine, dimethyl carbamoyl chloride, dimethyl formamide, 1,1-dimethyl hydrazine, dimethyl phthalate, dimethyl sulfate, 4,6-dinitro-o-cresol, and salts, 2,4-dinitrophenol, 2,4-dinitrotoluene, 1,4-dioxane (1,4-diethyleneoxide), 1,2-diphenylhydrazine, epichlorohydrin (1-chloro-2,3-epoxypropane), 1,2-epoxybutane, ethyl acrylate, ethyl benzene, ethyl carbamate (urethane), ethyl chloride (chloroethane), ethylene dibromide (dibromoethane), ethylene dichloride (1,2-dichloroethane), ethylene glycol, ethylene imine (aziridine), ethylene oxide, ethylene thiourea, ethylidene dichloride (1,1-dichloroethane), formaldehyde, heptachlor, hexachlorobenzene, hexachlorobutadiene, hexachlorocyclopentadiene, hexachloroethane, hexamethylene-1,6-diisocyanate, hexamethylphosphoramide, hexane, hydrazine, hydrochloric acid, hydrogen fluoride (hydrofluoric acid), hydrogen sulfide (see modification), hydroquinone, isophorone, lindane (all isomers), maleic anhydride, methanol, methoxychlor, methyl bromide (bromomethane), methyl chloride (chloromethane), methyl chloroform (1,1,1-trichloroethane), methyl ethyl ketone (2-butanone)(see modification), methyl hydrazine, methyl iodide (iodomethane), methyl isobutyl ketone (hexone), methyl isocyanate, methyl methacrylate, methyl tert butyl ether, 4,4-methylene bis(2-chloroaniline), methylene chloride (dichloromethane), methylene diphenyl diisocyanate (mdi), 4,4'-methylenedianiline, naphthalene, nitrobenzene, 4-nitrobiphenyl, a nitrogen oxide, 4-nitrophenol, 2-nitropropane, n-nitroso-n-methylurea, n-nitrosodimethylamine, n-nitrosomorpholine, ozone, parathion, pentachloronitrobenzene (quintobenzene), pentachlorophenol, phenol, p-phenylenediamine, phosgene, phosphine, phosphorus, phthalic anhydride, polychlorinated biphenyls (aroclors), 1,3-propane sultone, beta-propiolactone, propionaldehyde, propoxur (baygon), propylene dichloride (1,2-dichloropropane), propylene oxide, 1,2-propyleneimine (2-methyl aziridine), quinoline, quinone, styrene, styrene oxide, sulfur dioxide, 2,3,7,8-tetrachlorodibenzo-p-dioxin, 1,1,2,2-tetrachloroethane, tetrachloroethylene (perchloroethylene), titanium tetrachloride, toluene, 2,4-toluene diamine, 2,4-toluene diisocyanate, o-toluidine, toxaphene (chlorinated camphene), 1,2,4-trichlorobenzene, 1,1,2-trichloroethane, trichloroethylene, 2,4,5-trichlorophenol, 2,4,6-trichlorophenol, triethylamine, trifluralin, 2,2,4-trimethylpentane, vinyl acetate, vinyl bromide, vinyl chloride, vinylidene chloride (1,1-dichloroethylene), xylenes (isomers and mixture), o-xylenes, m-xylenes, p-xylenes, or any other foreign substance that may become into contact with the respiratory system of a mammal.

An exposure regimen for an agent or complex stimulus should reflect the range and circumstances of exposure in everyday settings. A set of standard exposure regimens can be designed to be applied systematically to well-defined experimental systems. Each assay could be designed to collect time and dose-dependent data to capture both early and late events and ensure a representative dose range is covered. Furthermore, the process of exposing the agent to the tissue may be the same as or different from the process by which exposure would occur to an organism. For example, to expose a tissue to an airborne agent, any number of techniques may be used, such as spraying the agent onto the tissue, storing the tissue and the agent in a confined space, or bringing the tissue into contact with the agent in an alternative form, such as in a solution or via suspension. However, it will be understood by one of skill in the art that the systems and methods described herein may be adapted and modified as is appropriate for the application being addressed and that the systems and methods designed herein may be employed in other suitable applications, and that such other additions and modifications will not depart from the scope thereof.

It is desirable to quantitatively and qualitatively assess an amount of injury or damage to tissue in the respiratory tract of an organism. In an example, following exposure to CS, the field of tissue injury occurs in not only lung tissue, but also in nasal tissue and tissues along the airway. In this case, it may be desirable to use tissue from the upper respiratory tract (such as nasal tissue or buccal tissue) as the surrogate biological tissue and tissue from the lower respiratory tract (such as lung tissue) as the target biological tissue. This may be desirable because tissue from the upper respiratory tract may be easier or cheaper to obtain than tissue from the lower respiratory tract. In this case, the surrogate biological tissue from the upper respiratory tract is used as a proxy to assess network perturbations or backbone activity values of the target biological tissue from the lower respiratory tract.

In one example, the surrogate biological tissue is an in vitro organotypic tissue culture from a tissue (from the respiratory tract, for example), and the sample of the target biological tissue includes in vivo data recorded from the same tissue. As an example, the tissue may be bronchial tissue or nasal tissue, and correlations between in vitro data and in vivo data may be observed for one or both tissues. By enabling a user to use a surrogate biological tissue as a proxy for a target biological tissue, in vitro data from a sample of biological tissue may be substituted for in vivo data, and advantageously, live animal testing may be reduced. The sources of samples of biological tissues include but are not limited to smokers, users of tobacco products, never-smokers, smokers who quit smoking, human patients with respiratory diseases, human chronic obstructive pulmonary disease (COPD) patients, and animal models of human respiratory diseases such as COPD.

In another example, correlations between a first biological tissue and a second biological tissue are observed, and correlations between the second biological tissue and the third biological tissue are also observed. In this case, the first biological tissue is correlated with the third biological tissue. In an example, the first biological tissue is in vitro data, and the second biological tissue is in vivo data, where the first and second biological tissues are recorded from the same region (nasal tissue, for example). The third biological tissue may be in vitro data or in vivo data obtained from another region (lung tissue, for example). In this case, all three biological tissues may be correlated, and any pair of biological tissues from the three biological tissues may be used as the surrogate biological tissue and the target biological tissue.

FIG. 1 depicts an example of a computer network and database structure that may be used to implement the systems and methods disclosed herein. FIG. 1 is a block diagram of a computerized system 100 for performing evaluation of a perturbation of a xenobiotic metabolism network model, according to an illustrative implementation. The system 100 includes a server 104, a user device 108, a network model database 106, and a correlations database 107 connected over a computer network 102. The server 104 includes a processor 105, and the user device 108 includes a processor 110 and a user interface 112. As used herein, the term "processor" or "computing device" refers to one or more computers, microprocessors, logic devices, servers, or other devices configured with hardware, firmware, and software to carry out one or more of the computerized techniques described herein. Processors and processing devices may also include one or more memory devices for storing inputs, outputs, and data that is currently being processed. An illustrative computing device 300, which may be used to implement any of the processors and servers described herein, is described in detail below with reference to FIG. 3. As used herein, "user interface" includes, without limitation, any suitable combination of one or more input devices (e.g., keypads, touch screens, trackballs, voice recognition systems, etc.) and/or one or more output devices (e.g., visual displays, speakers, tactile displays, printing devices, etc.). As used herein, "user device" includes, without limitation, any suitable combination of one or more devices configured with hardware, firmware, and software to carry out one or more computerized actions or techniques described herein. Examples of user devices include, without limitation, personal computers, laptops, and mobile devices (such as smartphones, tablet computers, etc.). Only one server, one user device, and two databases are shown in FIG. 1 to avoid complicating the drawing, but one of ordinary skill in the art will understand that the system 100 may support multiple servers and any number of databases or user devices.

The network model database 106 is a database that includes data representative of a network model and elements of the network model. For example, when the network model is a model of a biological system, the representation of the network model may be in the form of one or more statements in BEL. The BEL statements may provide an indication of a relationship between two nodes (the subject and the object, for example) of the network. The network model database 106 may store backbone nodes and measurable nodes separately. For example, the network model database 106 may store a set of backbone nodes in one part of the database, and the measurable nodes may be stored in another part of the database. Edges between nodes may be stored in the database with the set of backbone nodes, the set of measurable nodes, or separately, as a set of pointers for connecting two nodes. Furthermore, edges may be associated with a directional value, such as a +1 or −1 that indicates whether a causal relationship between two nodes is a causal increase relationship or a causal decrease relationship.

The correlations database 107 is a database that includes data representative of correlations between two tissues. For example, the correlation may correspond to a correlation between the expected perturbations of a target tissue and perturbations of a surrogate tissue, in response to exposure to an agent. In particular, the target tissue may be in vivo data collected from one area, such as one part of the respiratory tract (i.e., lung tissue or bronchial tissue, for example), and the surrogate tissue may be in vivo data collected from another area or another part of the respiratory tract (i.e., nasal tissue or buccal tissue, for example). In another example, the target tissue may be organotypic in vitro data collected from one area and the surrogate tissue may be organotypic in vitro data collected from another area. In yet another example, the target tissue may be in vivo data collected from one area, and the surrogate tissue may be organotypic in vitro data collected from the same area. In any of these examples, the correlation database 107 stores an indication that the expected perturbation or response of two datasets are expected to be correlated. In addition, the correlation database 107 may further store other parameters such as a set of linear regression parameters, a correlation score, or both, for each correlation. In particular, the set of linear regression parameters indicates how the two datasets are correlated and may include a y-intercept and a slope of the linear regression. The correlation score may indicate a strength of the correlation, and may be a correlation coefficient, for example.

Figure 2:
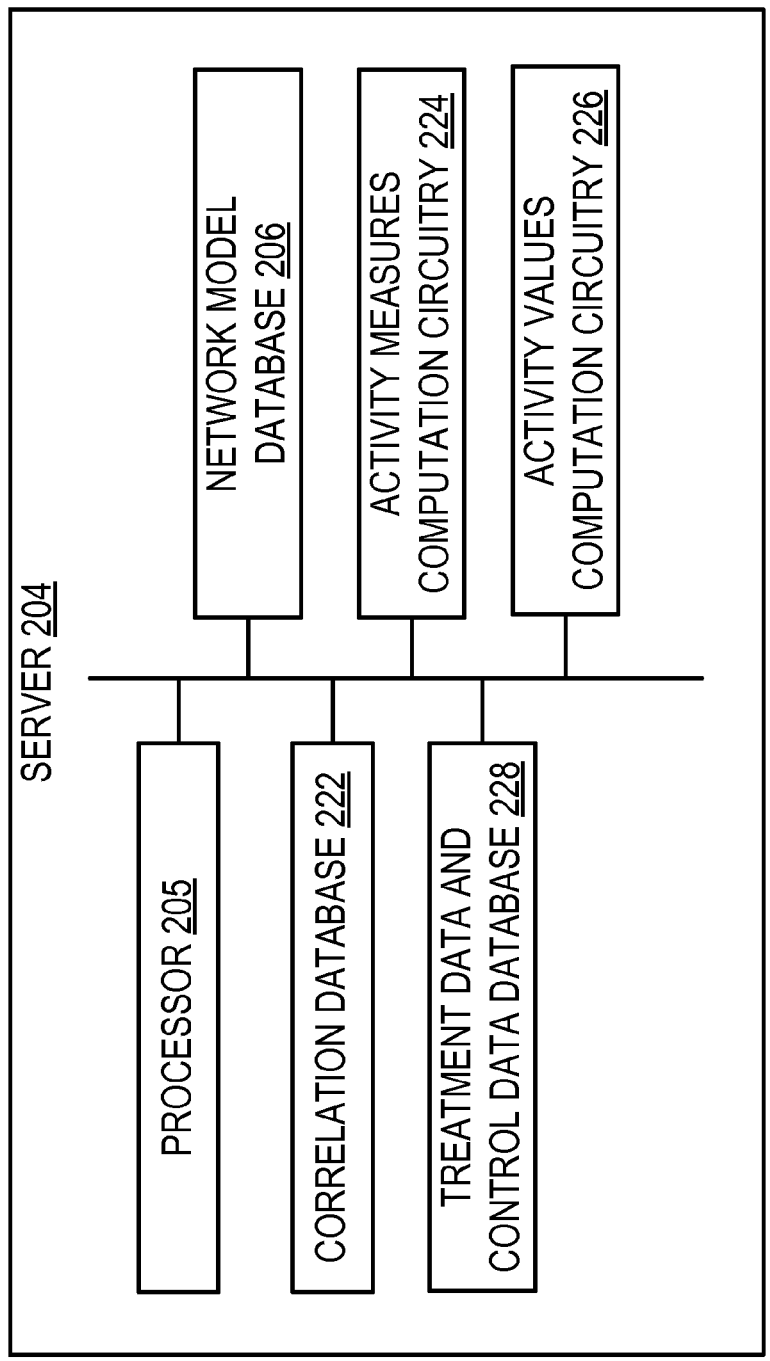
FIG. 2 depicts a block diagram of a server.

The components of the system 100 of FIG. 1 may be arranged, distributed, and combined in any of a number of ways. For example, a computerized system may be used that distributes the components of system 100 over multiple processing and storage devices connected via the network 102. Such an implementation may be appropriate for distributed computing over multiple communication systems including wireless and wired communication systems that share access to a common network resource. In some implementations, the system 100 is implemented in a cloud computing environment in which one or more of the components are provided by different processing and storage services connected via the Internet or other communications system. The server 104 may be, for example, one or more virtual servers instantiated in a cloud computing environment. In some implementations, the server 104 is combined with the network model database 106 into one component, an example of which is described in relation to FIG. 2. In particular, FIG. 2 is a block diagram of a server 204 that performs any of the functions described herein. The server 204 includes a processor 205, a correlation database 222, a treatment data and control data database 228, a network model database 206, activity measures computation circuitry 224, and activity values computation circuitry 226, all connected over a bus.

Figure 3:
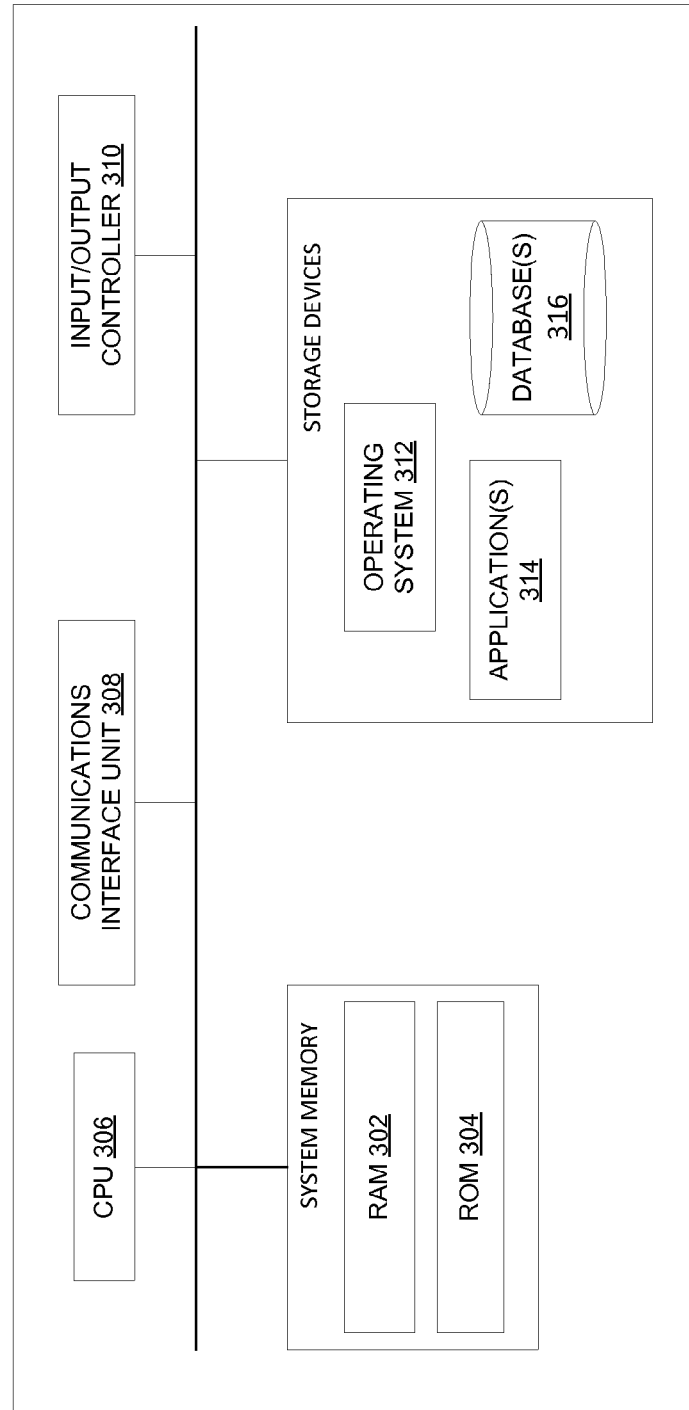
FIG. 3 depicts a block diagram of a computing device.

FIG. 3 is a block diagram of a computing device, such as any of the components of system 100 of FIG. 1 for performing processes described herein. Each of the components of system 100, including the user device 108, the network model database 106, the correlations database 107, or the server 104 may be implemented on one or more computing devices 300. In certain aspects, a plurality of the above-components and databases may be included within one computing device 300. In certain implementations, a component and a database may be implemented across several computing devices 300.

The computing device 300 comprises at least one communications interface unit, an input/output controller 310, system memory, and one or more data storage devices. The system memory includes at least one random access memory (RAM 302) and at least one read-only memory (ROM 304). All of these elements are in communication with a central processing unit (CPU 306) to facilitate the operation of the computing device 300. The computing device 300 may be configured in many different ways. For example, the computing device 300 may be a conventional standalone computer or alternatively, the functions of computing device 300 may be distributed across multiple computer systems and architectures. The computing device 300 may be configured to perform some or all of modeling, scoring and aggregating operations. In FIG. 3, the computing device 300 is linked, via network or local network, to other servers or systems.

The computing device 300 may be configured in a distributed architecture, wherein databases and processors are housed in separate units or locations. Some such units perform primary processing functions and contain at a minimum a general controller or a processor and a system memory. In such an aspect, each of these units is attached via the communications interface unit 308 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 306 comprises a processor, such as one or more conventional microprocessors and one or more supplementary co-processors such as math co-processors for offloading workload from the CPU 306. The CPU 306 is in communication with the communications interface unit 308 and the input/output controller 310, through which the CPU 306 communicates with other devices such as other servers, user terminals, or devices. The communications interface unit 308 and the input/output controller 310 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices.

The CPU 306 is also in communication with the data storage device. The data storage device may comprise an appropriate combination of magnetic, optical or semiconductor memory, and may include, for example, RAM 302, ROM 304, flash drive, an optical disc such as a compact disc or a hard disk or drive. The CPU 306 and the data storage device each may be, for example, located entirely within a single computer or other computing device; or connected to each other by a communication medium, such as a USB port, serial port cable, a coaxial cable, an Ethernet type cable, a telephone line, a radio frequency transceiver or other similar wireless or wired medium or combination of the foregoing. For example, the CPU 306 may be connected to the data storage device via the communications interface unit 308. The CPU 306 may be configured to perform one or more particular processing functions.

The data storage device may store, for example, (i) an operating system 312 for the computing device 300; (ii) one or more applications 314 (e.g., computer program code or a computer program product) adapted to direct the CPU 306 in accordance with the systems and methods described here, and particularly in accordance with the processes described in detail with regard to the CPU 306; or (iii) database(s) 316 adapted to store information that may be utilized to store information required by the program. In some aspects, the database(s) includes a database storing experimental data, and published literature models.

The operating system 312 and applications 314 may be stored, for example, in a compressed, an uncompiled and an encrypted format, and may include computer program code. The instructions of the program may be read into a main memory of the processor from a computer-readable medium other than the data storage device, such as from the ROM 304 or from the RAM 302. While execution of sequences of instructions in the program causes the CPU 306 to perform the process steps described herein, hard-wired circuitry may be used in place of, or in combination with, software instructions for implementation of the processes of the present disclosure. Thus, the systems and methods described are not limited to any specific combination of hardware and software.

Suitable computer program code may be provided for performing one or more functions described herein. The program also may include program elements such as an operating system 312, a database management system and "device drivers" that allow the processor to interface with computer peripheral devices (e.g., a video display, a keyboard, a computer mouse, etc.) via the input/output controller 310.

The term "computer-readable medium" as used herein refers to any non-transitory medium that provides or participates in providing instructions to the processor of the computing device 300 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer may read.

Various forms of computer readable media may be involved in carrying one or more sequences of one or more instructions to the CPU 306 (or any other processor of a device described herein) for execution. For example, the instructions may initially be borne on a magnetic disk of a remote computer (not shown). The remote computer may load the instructions into its dynamic memory and send the instructions over an Ethernet connection, cable line, or even telephone line using a modem. A communications device local to a computing device 300 (e.g., a server) may receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

FIG. 9 shows a flow chart of a method 900 for evaluating the perturbation of a xenobiotic metabolism network model. In particular, the method 900 quantifies the perturbation of a target biological tissue in response to exposure to an agent. The method 900 includes the steps of storing data representative of a computational causal network model of xenobiotic metabolism (902), receiving a set of contrast data corresponding to a difference between treatment data and control data, the treatment data being representative of a response of a sample of surrogate biological tissue to exposure to an agent (904), and determining activity values for at least some of the backbone nodes based on the biological activity measures of at least some of the measurable nodes and the computational causal network model (906). The method 900 further includes computing a score indicating a perturbation of the sample of the surrogate biological tissue in response to exposure to the agent (908), identifying a correlation between the perturbation of the target biological tissue in response to the agent and the perturbation of the surrogate biological tissue in response to the agent (910), and providing the score to indicate the perturbation of the target biological tissue in response to the agent (912).

At 902, data representative of a computational causal network model of xenobiotic metabolism is stored in a database such as network model database 106. In particular, the computational causal network model includes set of measurable nodes representative of biological activities and a set of backbone nodes representative of biological activities. At least some of the biological activities of the backbone nodes are related to xenobiotic metabolism. Furthermore, the computational causal network model also includes a set of edges, where each edge is representative of a causal relationship between nodes. The set of backbone nodes, measurable nodes, and edges may include those shown in Table 1, 2, or a subset thereof. In particular, at least one of the backbone nodes corresponds to AHR or a transcriptional activity of AHR. As described herein, the computational causal network model may be constructed using RCR.

At 904, a set of contrast data corresponding to a difference between treatment data and control data is received. The treatment data is representative of a response of a sample of surrogate biological tissue to exposure to an agent, and the control data is representative of a response of the sample of the surrogate biological tissue to non-exposure to the agent or a control condition. The set of contrast data includes biological activity measures for at least some of the nodes in the set of measurable nodes. For example, the biological activity measures may correspond to differences in gene expression levels (of the measurable nodes) between the treatment data and the control data, and thus represent a change in activity levels at a set of the measurable nodes in response to exposure to the agent.

At 906, activity values are determined for at least some of the backbone nodes based on the biological activity measures of at least some of the measurable nodes and the computational causal network model. As described herein, the activity values of the backbone nodes are inferred from the biological activity measures of the measurable nodes and the connections between the measurable nodes and the backbone nodes in the network model.

At 908, a score is computed that indicates a perturbation of the sample of the surrogate biological tissue in response to exposure to the agent. As described above, the score may correspond to an overall perturbation evaluation, such as an NPA score, an IPA score, the GSEA score, a strength score, a combination thereof, or any other suitable score for assessing the perturbation of a network model in response to an agent. In particular, the score may correspond to the activity value of a single backbone node, or the score may be computed based on the activity values of multiple backbone nodes. In an example, the score may be computed as a quadratic function of the biological activity measures for the at least some of the measurable nodes.

At 910, a correlation is identified between the perturbation of the target biological tissue in response to the agent and the perturbation of the surrogate biological tissue in response to the agent. Identifying the correlation includes determining that the computational causal network model of xenobiotic metabolism is applicable to both the perturbation of the target biological tissue in response to the agent and the perturbation of the surrogate biological tissue in response to the agent. In particular, a correlations database such as the correlations database 107 may be probed to identify whether such a correlation between the target biological tissue and the surrogate biological tissue exists. If such a correlation exists, the parameters of the correlation (such as the linear regression parameters or the strength of the correlation, for example) may further be determined. In an example, the score is modified based on the correlation. For example, the score may be modified to generate a modified score based on one or more of the linear regression parameters. In particular, when the linear regression parameters include a slope and a y-intercept or an x-intercept, the linear regression parameters may be used to offset the score by the y- or x-intercept, scale the score by the slope, or both. In general, modification of the score may be performed in any suitable manner in order to obtain a modified score that is representative of a predicted perturbation of the target biological tissue.

At 912, the score is provided to indicate the perturbation of the target biological tissue in response to the agent. In particular, when a correlation is identified between the target biological tissue and the surrogate biological tissue, the score (which was evaluated with respect to the surrogate biological tissue) may be provided as an indication of the perturbation of the target biological tissue. In some embodiments, the score may be modified based on the parameters of the identified correlation (such as being scaled or being offset by values determined from the linear regression parameters, for example), and the modified score may be provided.

In an example, the perturbation of the target biological tissue is representative of biological activity measures expected to be observed from in vivo data sampled from the target biological tissue. The perturbation of the surrogate biological tissue is representative of biological activity measures observed from in vivo or organotypic in vitro data sampled from the surrogate biological tissue, and wherein the target biological tissue is different from the surrogate biological tissue.

In another example, the perturbation of the target biological tissue is representative of biological activity measures expected to be observed from organotypic in vitro data sampled from the target biological tissue. In this case, the perturbation of the surrogate biological sample is representative of biological activity measures observed from organotypic in vitro data sampled from the surrogate biological tissue.

In an example, the target biological tissue, the surrogate biological tissue, or both are selected from the group consisting of: lung tissue, nasal tissue, bronchial tissue, buccal tissue, upper respiratory tract, lower respiratory tract, and epithelial cells. In an example, the agent is selected from the group consisting of: cigarette smoke, carbon monoxide, soot, diesel exhaust particles, particulate matter, and air pollution. When the agent is a drug, the agent may be sprayed on an organotypic culture in vitro in order to expose the surrogate biological tissue to the agent.

In an example, the computational causal network model is of mammalian xenobiotic metabolism in the respiratory system, and the target biological tissue and the surrogate biological tissue are sampled from mammalian tissue. The mammalian xenobiotic metabolism may be a part of the respiratory system. Furthermore, the computational causal network model may be representative of human xenobiotic metabolism, and the target biological tissue and the surrogate biological tissue are sampled from human tissue.

Various methods of obtaining gene expression level measurements from a tissue may be used, including in vitro and in vivo measurements. Described herein are methods for obtaining measurements from tissue cultures, the data for which are shown and described in relation to FIGS. 5-8.

In some embodiments, measurements of expression levels (such as activity measures of measurable nodes, for example) are taken from organotypic tissue cultures. In an example, measurements were obtained from organotypic tissue cultures for the data shown in FIGS. 7A to 7D and FIGS. 8A to 8D. In particular, MucilAir™-human fibroblasts-bronchial and MucilAir™-human fibroblast-nasal full-thickness tissue models based on primary human respiratory epithelial cells co-cultured with primary human airway fibroblasts were purchased from Epithelix Sárl (Geneva, Switzerland) and maintained according to the manufacturer's protocol. MucilAir™ model is a ready-to-use 3D model of differentiated human epithelium [Huang S, Wiszniewski L, Constant S: The use of in vitro 3D cell models in drug development for respiratory diseases. *Tech December* 2011.]. The organotypic tissue cultures are primary human epithelial cells isolated from healthy, non-smoking, Caucasian donors that are reconstituted using fibroblasts. Co-culture of fibroblasts has been shown to contribute to the growth and differentiation of epithelial cells in 3D cultures [Parrinello S, Coppe J-P, Krtolica A, Campisi J: Stromal-epithelial interactions in aging and cancer: senescent fibroblasts alter epithelial cell differentiation. *Journal of cell science* 2005, 118(3):485-496.]. The bronchial epithelial cells were obtained from one donor, and the nasal epithelial cells were obtained from another donor. Quality control assessments were performed on both models (data not shown). The tissue models were cultured at the air-liquid interface in 0.7 ml media in cell culture inserts (24-well format). The organotypic models were maintained at 37° C. for 14 days at the air-liquid interface with fresh medium added every 2 days.

The respiratory organotypic tissue culture models as described herein may be exposed to cigarette smoke (CS). In particular, for the data shown in FIGS. 7A-7D and FIGS. 8A-8D, after cell culture models grown in culture for 2-3 days, the tissues (in triplicate) were exposed at the air-liquid interface to 16% (vol/vol) mainstream CS exposure (a total of 4 cigarettes, 3R4F) with 1 hour rest between each cigarette and 60% humidified air in the Vitrocell systems (Waldkirch, Germany). The 60% humidified air exposure was used as a control exposure. The Total Particulate Matter (TPM) inside the exposure chamber has been measured for each CS concentration (the mean TPM deposition measured after each cigarette was 2842.4 ng/cm2 SEM=570.7, N=24). The reference cigarette 3R4F was obtained from the University of Kentucky and smoked on the 30-port carousel smoking machine (SM2000, Philip Morris, Int.) according to the Health Canada regimen [Health Canada. Determination of "Tar", Nicotine and Carbon Monoxide in Mainstream Tobacco Smoke. 1999.]. After exposure, the organotypic models were incubated with fresh culture medium immediately (0 h post-exposure). Additionally various durations of post-exposure were implemented (4, 24, and 48 h) before tissues were harvested for further analyses.

Exposed tissues (n=3) at 0, 4, 24 and 48 h post-exposure time were washed 3 times with ice-cold PBS and subsequently lysed using Qiazol lysis reagent (miRNeasy Mini Kit, Qiagen) and frozen at −80° C. for up to 1 week. The miRNeasy Mini Kit was used for the extraction and purification of mRNA. Total RNA quantity was measured using NanoDrop ND1000 and qualitatively verified using an Agilent 2100 Bioanalyzer profile (A RIN number greater than 8). For the mRNA analysis, total RNA (100 ng) was processed according to the GeneChip HT 3'IVT Express User Manual (Affymetrix). Genechip Human Genome U133 Plus 2 Arrays were used for microarray hybridization.

In some embodiments, microarray data processing is performed. In particular, data processing and scoring methods were implemented using the R statistical environment version 2.14 [R Development Core Team: R: A Language and Environment for Statistical Computing; 2009.]. Raw RNA expression data were analyzed using the affy and limma packages of the Bioconductor suite of microarray analysis tools (version 2.9) available in the R statistical environment [Gentleman R: Bioinformatics and computational biology solutions using R and Bioconductor. New York: Springer Science+Business Media; 2005; Gentleman R C, Carey V J, Bates D M, Bolstad B, Dettling M, Dudoit S, Ellis B, Gautier L, Ge Y, Gentry J et al: Bioconductor: open software development for computational biology and bioinformatics. *Genome Biol* 2004, 5(10):R80.]. Robust Multichip Average (GCRMA) background correction and quantile normalization were used to generate probe set expression values [Irizarry R A, Hobbs B, Collin F, Beazer-Barclay Y D, Antonellis K J, Scherf U, Speed T P: Exploration, normalization, and summaries of high density oligonucleotide array probe level data. *Biostatistics* 2003, 4(2):249-264.]. For each data set, an overall linear model was fitted to the data for the specific contrasts of interest (pertaining to the comparisons of "treated" and "control" conditions) generating raw p-values for each probe set on the microarray, which were further adjusted using the Benjamini-Hochberg procedure. A blocking factor (the exposure plate) from the experiment design was accounted in the model for the data processing for the organotypic bronchial and nasal tissue.

The activity of CYP1A1 and CYP1B1 was measured using non-lytic P450-Glo assays (CYP1A1 assay cat #: V8752; CYP1B1 assay cat # V8762; Promega) based on luminescence at the 48 hours of CS post-exposure on the human organotypic nasal and bronchial models. The assay is performed according to the manufacturer's recommendations. Briefly, both nasal and bronchial tissues were incubated in medium with luminogenic CYP-Glo substrate, such as luciferin-CEE for 3 h (CYP1A1 and CYP1B1), to produce a luciferin product that can be quantified in the supernatant by a light-generating reaction upon the addition of luciferin detection reagent.

Figure 5A:
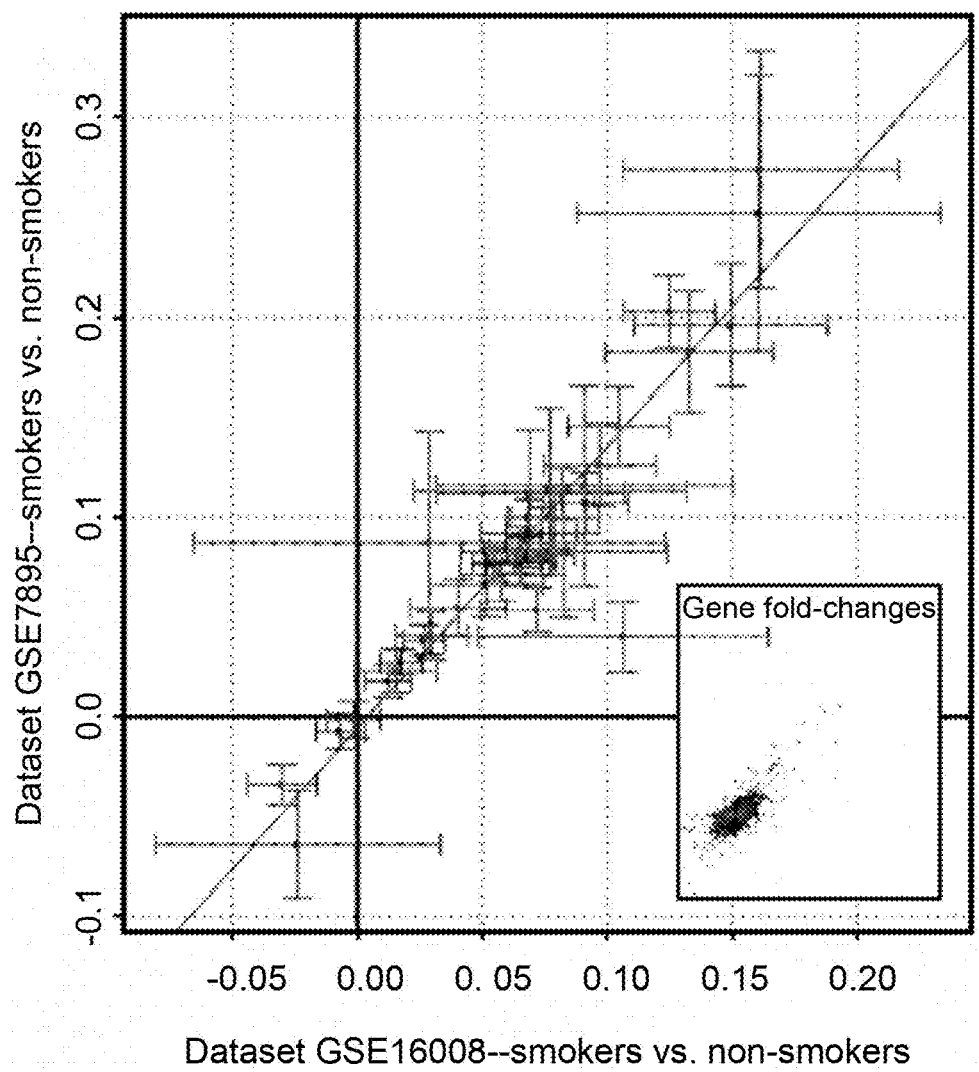
FIGS. 5A, 5B, and 5C depict the correlation of the activity values of backbone nodes in a xenobiotic metabolism network model.
Figure 5B:
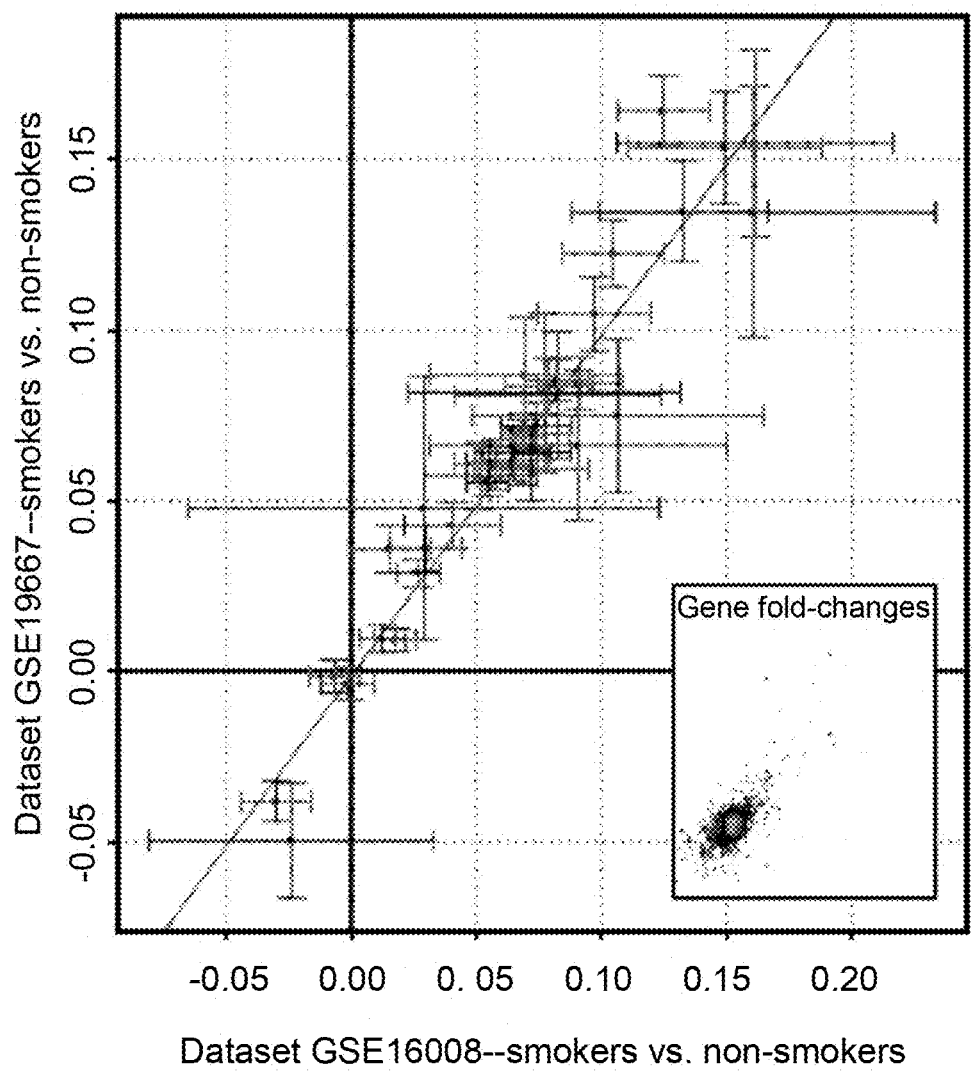
Figure 5C:
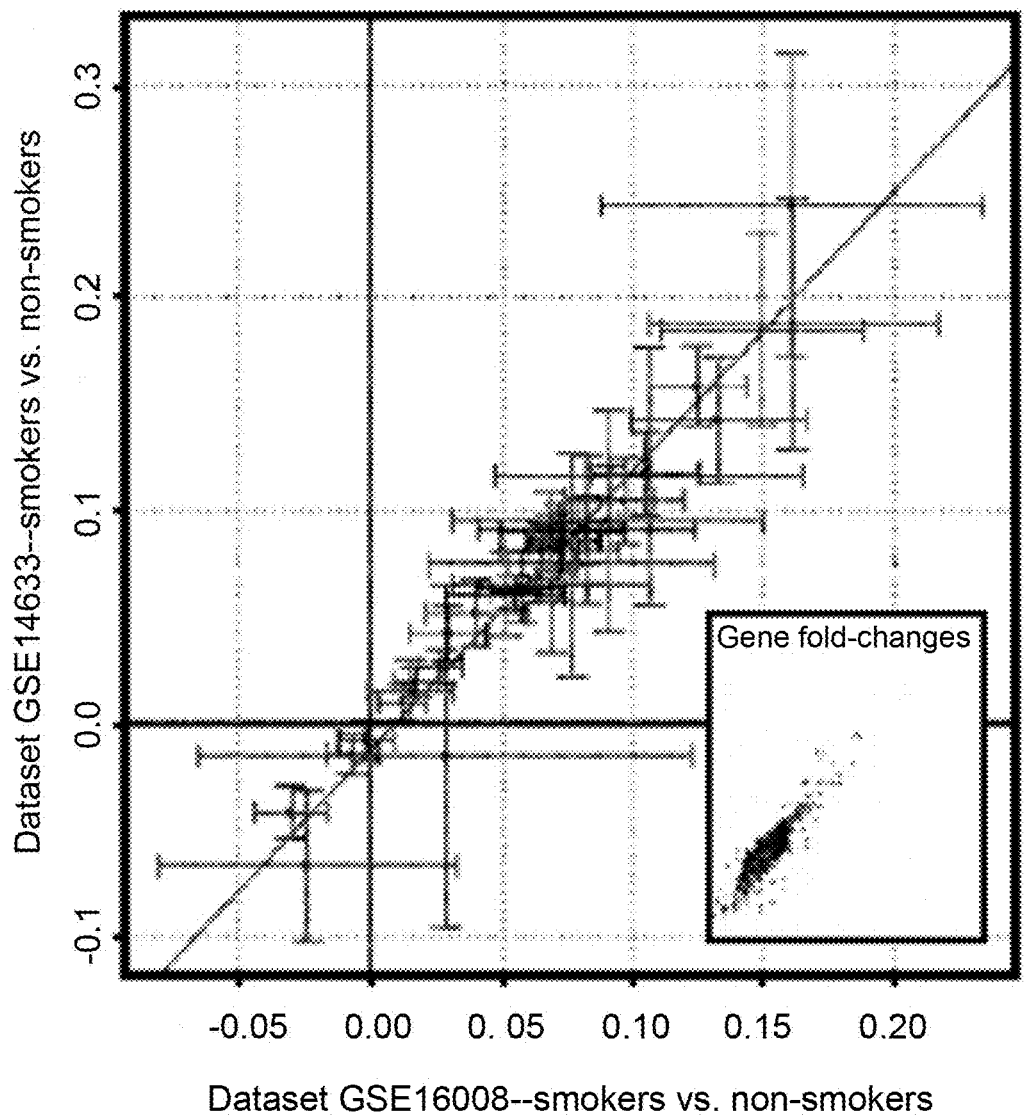

In a first example, a correlation was observed in the activity values of the backbone nodes in the xenobiotic metabolism network model using the network perturbation amplitude (NPA) method between four datasets for human nasal and bronchial epithelium samples obtained from healthy individuals who are current smokers and from healthy individuals who have never smoked. FIGS. 5A, 5B, and 5C show the correlations of the activity values of the backbone nodes between the GSE16008 dataset and three other data sets (the GSE7895 dataset(FIG. 5A), the GSE19667 dataset (FIG. 5B), and the GSE14633 dataset (FIG. 5C)). The GSE16008 dataset includes gene expression data measured from nasal and bronchial epithelium samples obtained from smokers and non-smokers. The bronchial epithelial cells were collected by bronchoscopy, while the nasal epithelial cells were collected by brushing the inferior turbinate [Zhang X, Sebastiani P, Liu G, Schembri F, Zhang X, Dumas Y M, Langer E M, Alekseyev Y, O'Connor G T, Brooks D R et al: Similarities and differences between smoking-related gene expression in nasal and bronchial epithelium. *Physiological genomics* 2010, 41(1):1-8.]. Each of the other three datasets (GSE7895 [Beane J, Sebastiani P, Liu G, Brody J S, Lenburg M E, Spira A: Reversible and permanent effects of tobacco smoke exposure on airway epithelial gene expression. *Genome Biol* 2007, 8(9):R201.], GSE19667 [Strulovici-Barel Y, Omberg L, O'Mahony M, Gordon C, Hollmann C, Tilley A E, Salit J, Mezey J, Harvey B G, Crystal R G: Threshold of biologic responses of the small airway epithelium to low levels of tobacco smoke. *American journal of respiratory and critical care medicine* 2010, 182(12):1524-1532.], and GSE14633 [Schembri F, Sridhar S, Perdomo C, Gustafson A M, Zhang X, Ergun A, Lu J, Liu G, Zhang X, Bowers J et al: MicroRNAs as modulators of smoking-induced gene expression changes in human airway epithelium. *Proc Natl Acad Sci USA* 2009, 106(7):2319-2324.]) includes gene expression data measured from bronchial epithelium samples obtained by bronchoscopy from smokers and non-smokers.

FIGS. 5A, 5B, and 5C show the correlation of the activity values of the backbone nodes (also referred to as the differential network backbone values) in the xenobiotic metabolism network model (depicted in FIGS. 4A and 4B), using the NPA approach between the GSE16008 dataset and each of the other datasets. In particular, each data point in FIGS. 5A, 5B, and 5C represents a backbone node in the xenobiotic metabolism network model. The 95%-confidence interval of the differential network backbone values is shown for the two perturbations (axes). Solid diagonal lines show the linear regression line computed by least squares fit for each FIGS. 5A, 5B, and 5C. All the regression models were significant (P<0.05), and FIGS. 5A, 5B, and 5C illustrate the correlation of the fold-change of gene expressions.

In a second example, a correlation was observed between in vivo data collected from the nasal epithelium and in vivo data collected from the bronchial epithelium (GSE16008). FIG. 6A shows that the activity values of the backbone nodes (differential network backbone values) were well correlated between the in vivo bronchial and nasal brushing epithelia. Furthermore, the inset of FIG. 6A illustrates how the backbone node for AHR may be computed from gene expression data. In particular, each data point in FIG. 6A represents a backbone node in the xenobiotic metabolism network model. The diagonal line is the linear regression line computed by least squares fit with significant P-value <0.05. The 95%-confidence interval of the differential backbone values is shown for the two perturbations (axes). The inset of FIG. 6A shows an illustration of the expression of genes underneath the backbone node AHR.

FIG. 6B is a graphical illustration of the activity values of the backbone nodes (differential network backbone values) in the xenobiotic metabolism network model using the in vivo bronchial (left) and nasal (right) data. The different shades reflect the quantification of the backbone nodes derived from the NPA scoring technique that demonstrates the biological mechanisms pertaining to xenobiotic metabolism. Negative values indicate downregulation of the backbone node activity, and positive values indicate upregulation of the backbone node activity. The symbol * indicates significant P-values <0.05. The nature of the perturbation of the xenobiotic metabolism network model is reflected on the activity values of the backbone nodes and is similar between the bronchial and nasal epithelia. For example, cigarette smoking was associated with decreased activation of the aryl hydrocarbon receptor repressor (AHRR) in both the bronchial and nasal samples (FIG. 6B). AHRR is known to inhibit the binding of AHR to xenobiotic-responsive elements (XRE), thus suppressing the transcription of AHR-dependent genes, including CYP1A1, CYP1A2, and CYP1B1 [Stejskalova L, Vecerova L, Perez L M, Vrzal R, Dvorak Z, Nachtigal P, Pavek P: Aryl hydrocarbon receptor and aryl hydrocarbon nuclear translocator expression in human and rat placentas and transcription activity in human trophoblast cultures. *Toxicological sciences: an official journal of the Society of Toxicology* 2011, 123(1):26-36.]. Upregulation of the backbone activity values was consistently observed for these CYPs (FIG. 6B). As shown in FIG. 6B, the backbone nodes that have darker shading are those that contribute the most to the NPA score. For example, the darkest backbone nodes in FIG. 6B correspond to AHRR, 8-methyl-IQX, indurubin, AHR, curcurmin, NFE2L2, oxof (CYP2E1), and catof(NQO1), for example.

FIG. 6C shows the bar plots of the NPA scores for the xenobiotic metabolism network model for the bronchial (left) and for the nasal (right) samples. FIG. 6C also shows the companion statistics O* and K*, which both show significance, suggesting that both in vivo nasal and bronchial samples significantly demonstrate the biological mechanisms represented in the xenobiotic metabolism network model. Statistical significance of the perturbation of the xenobiotic metabolism network model in response to smoking are shown: * indicates significance of NPA scores (P-values <0.05) of the entire network level generated from the in vivo bronchial and nasal datasets. These results suggest that the nasal epithelium and the bronchial epithelium elicit similar xenobiotic responses upon being exposed to CS. The similar xenobiotic responses are reflected by the activity values of the backbone nodes in the xenobiotic metabolism network model. These results suggest that the nasal epithelium may be used as a surrogate sample of the bronchial epithelium for CS exposure. Furthermore, these results also support the notion that exposure to CS may result in similar responses or similar impacts on the tissues lining the respiratory tract [Steiling K, Ryan J, Brody J S, Spira A: The field of tissue injury in the lung and airway. *Cancer prevention research* (Philadelphia, Pa.) 2008, 1(6): 396-403.].

Figure 6D:
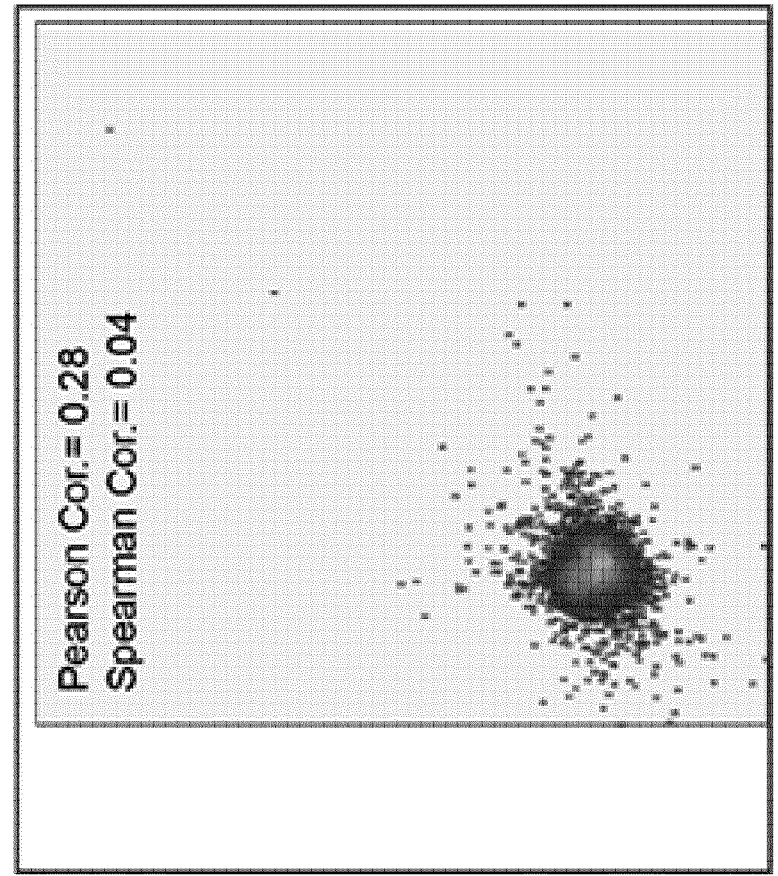
FIG. 6D depicts a lack of correlation at the backbone nodes at the level of the measurable nodes.

Moreover, unlike the correlation at the backbone nodes (i.e., functional layer), correlation at the level of the measurable nodes (i.e., transcriptional layer) was not observed (FIG. 6D). This indicates that the utilization of the NPA method using the xenobiotic metabolism network model that comprised of these two layers (i.e., functional and transcriptional layer) may facilitate a high-resolution comparison of high-throughput transcriptomic datasets.

In a third example, a correlation was observed between xenobiotic metabolism responses in in vitro organotypic bronchial and nasal epithelial tissues in response to exposure to CS. Development of a reliable in vitro system that mimics the condition in vivo can be challenging. Recently, organotypic culture of human cells have been developed and utilized to understand the normal biological processes [Karp P H, Moniger T, Weber S P, Nesselhauf T S, Launspach J L, Zabner J, Welsh M J: An in vitro model of differentiated human airway epithelia. *Methods Mol Biol* 2002, 188:115-137; Mathis C, Poussin C, Weisensee D, Gebel S, Hengstermann A, Sewer A, Belcastro V, Xiang Y, Ansari S, Wagner S: Human bronchial epithelial cells exposed in vitro to cigarette smoke at the air-liquid interface resemble bronchial epithelium from human smokers. *American Journal of Physiology-Lung Cellular and Molecular Physiology* 2013; Maunders H, Patwardhan S, Phillips J, Clack A, Richter A: Human bronchial epithelial cell transcriptome: gene expression changes following acute exposure to whole cigarette smoke in vitro. *Am J Physiol Lung Cell Mol Physiol* 2007, 292(5):L1248-1256; Pezzulo A A, Starner T D, Scheetz T E, Traver G L, Tilley A E, Harvey B G, Crystal R G, McCray P B, Jr., Zabner J: The air-liquid interface and use of primary cell cultures are important to recapitulate the transcriptional profile of in vivo airway epithelia. *Am J Physiol Lung Cell Mol Physiol* 2011, 300(1):L25-31; Bosse Y, Postma D S, Sin D D, Lamontagne M, Couture C, Gaudreault N, Joubert P, Wong V, Elliott M, van den Berge M et al: Molecular Signature of Smoking in Human Lung Tissues. *Cancer research* 2012, 72(15):3753-3763.]. In the present study, the network perturbation that was elicited in in vitro organotypic bronchial epithelium was compared to that for in vitro organotypic nasal epithelium that were repeatedly exposed to whole CS. The cells were immediately harvested after the last exposure (0 h post-exposure).

Figure 7A:
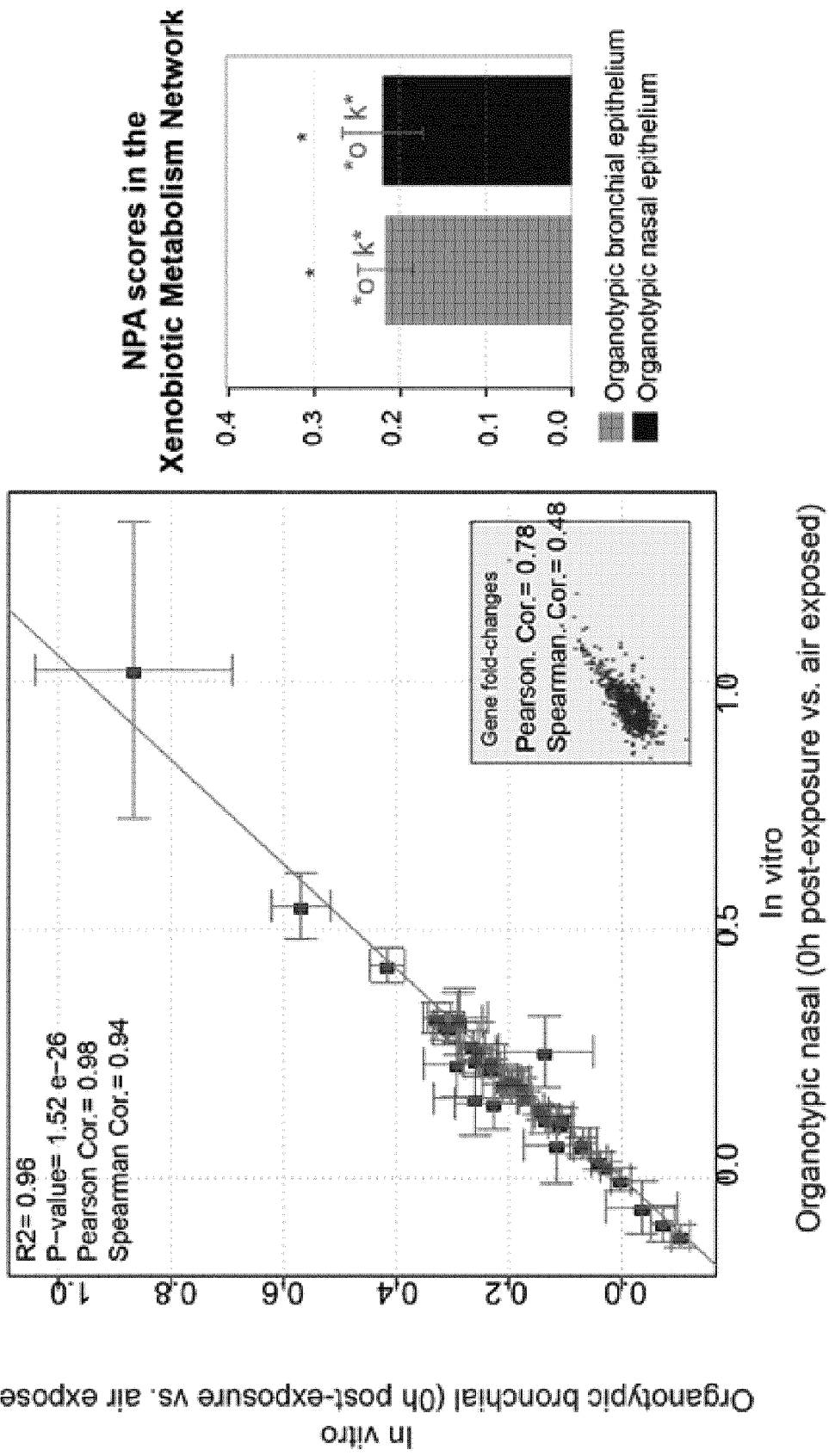
FIG. 7A depicts a correlation between activity values of backbone nodes for in vitro bronchial and nasal brushing data.

FIG. 7A shows that the activity values of the backbone nodes are well correlated between the in vitro bronchial and nasal brushing epithelia. Each data point in FIG. 7A represents a backbone node in the xenobiotic metabolism network model as indicated with the node labels. The diagonal line is the linear regression line computed by least squares fit with significant P-value <0.05. The 95%-confidence interval of activity values of the backbone nodes is shown for the two perturbations (axes). The inset of FIG. 7A illustrates the correlation between the fold-changes of the gene expression (correlation at the transcriptional layer).

The bar plot of NPA scores shows statistical significance of the perturbation of the xenobiotic metabolism network model in response to smoking are shown: * indicates significance of NPA scores of the entire network level generated from the in vitro bronchial and nasal datasets as well as their companion statistics O* and K* as described in Materials and methods (P-values <0.05). This comparability at the functional layer was in agreement with what was observed using the in vivo dataset. The bar plots (FIG. 7A) shows the NPA scores for the xenobiotic metabolism network model along with the companion statistics. These significant statistics suggest that both in vitro nasal and bronchial samples from the dataset significantly demonstrate the biological mechanisms represented in the xenobiotic metabolism network model.

Figure 7B:
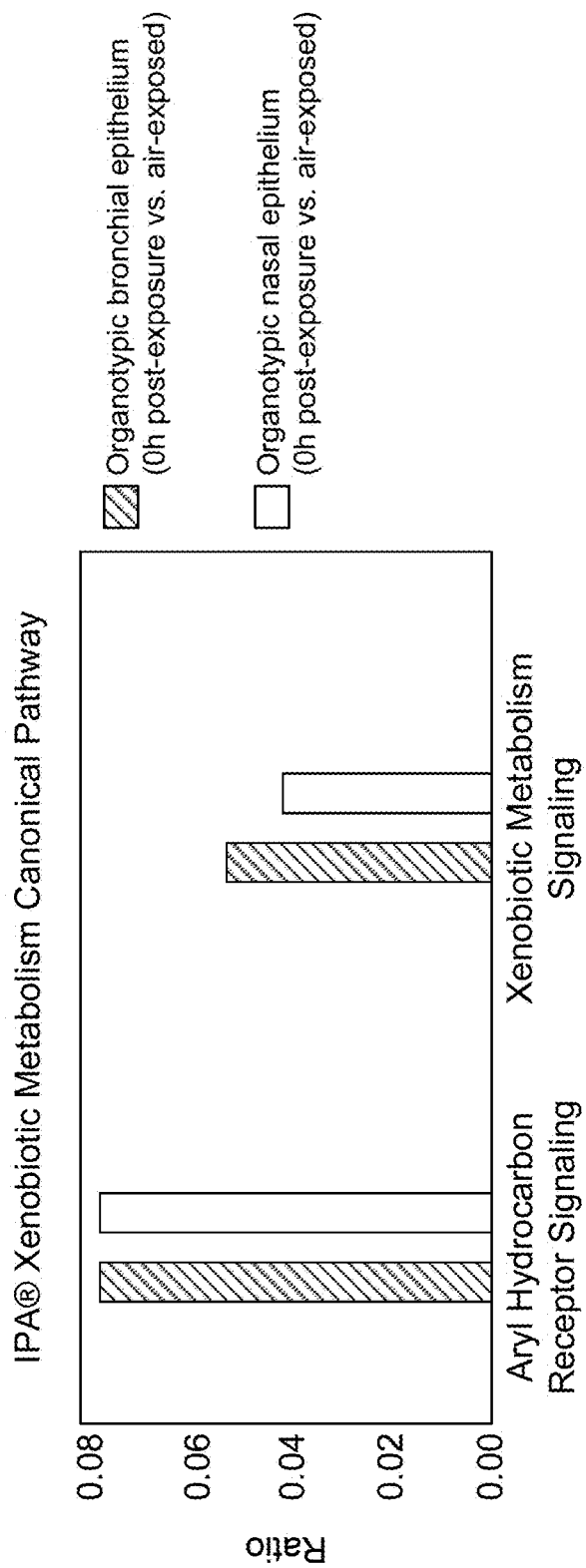
FIG. 7B depicts significant associations between the data and canonical pathways.

Furthermore, to investigate how the analysis using the xenobiotic metabolism network model compared to the commercially available IPA®'s data analysis and interpretation tool, the same datasets generated from the in vitro organotypic samples were uploaded to IPA®. According to the IPA®'s knowledge base, the xenobiotic metabolism canonical pathways consist of the AHR Signaling and the xenobiotic metabolism signaling. FIG. 7B shows significant associations between the datasets and the two IPA®'s canonical pathways within the category of "xenobiotic metabolism." The y-axis displays the ratio calculated as the number of genes in the associated pathways that meet cutoff criteria, divided by the total number of genes that make up that specific pathway. The taller the bars, the more genes were associated with the pathway. Representative pathways overlapped between the two datasets generated from the organotypic bronchial and nasal models. Similar associations to the two signaling pathways, which were indicated by the comparability of the ratios (FIG. 7B) were observed between the bronchial and nasal epithelia. This observation was in agreement with the NPA analyses using the network model (FIG. 7A).

Figure 7C:
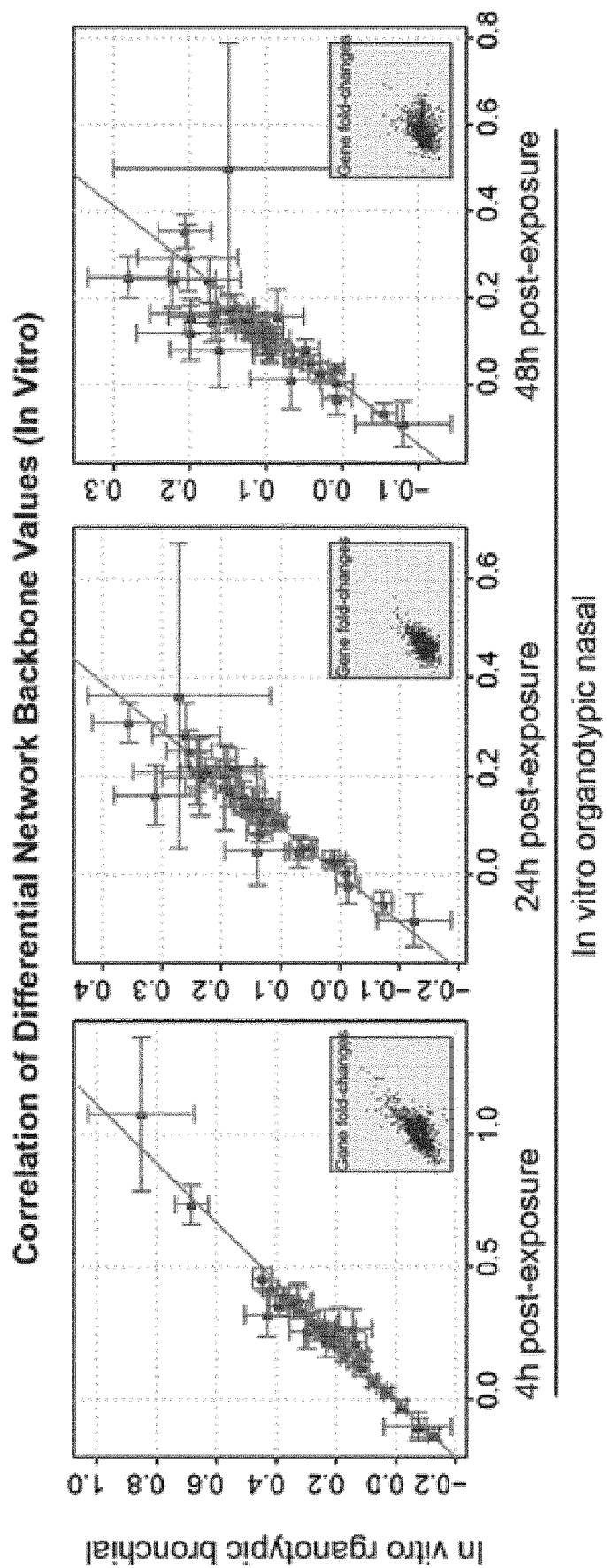
FIG. 7C depicts correlations between backbone values for in vitro organotypic nasal and bronchial data.

Additionally, the effects of various post-exposure time points were examined to assess the ability of cells to recover from exposure to CS. It was hypothesized that for a longer duration of post-exposure, less perturbation would be observed in the xenobiotic metabolism network model. Table 3 lists the Pearson correlation coefficients and Spearman correlation coefficients for the data shown in FIG. 7C. In particular, the activity values of the backbone nodes continue to be correlated between the bronchial and nasal epithelia at the 4, 24, and 48 h post-exposure times (FIG. 7C and Table 3). Nevertheless, the correlations were reduced as the duration of the post-exposure increased (FIG. 7C and Table 3). Each data point in FIG. 7C represents a backbone node in the xenobiotic metabolism network model as indicated with the node labels. The diagonal line is the linear regression line computed by least squares fit with significant P-value <0.05. The 95%-confidence interval of the differential backbone values is shown for the two perturbations (axes). The inset of FIG. 7C illustrates the correlation between the fold-changes of the gene expression (correlation at the transcriptional layer).

Figure 7D:
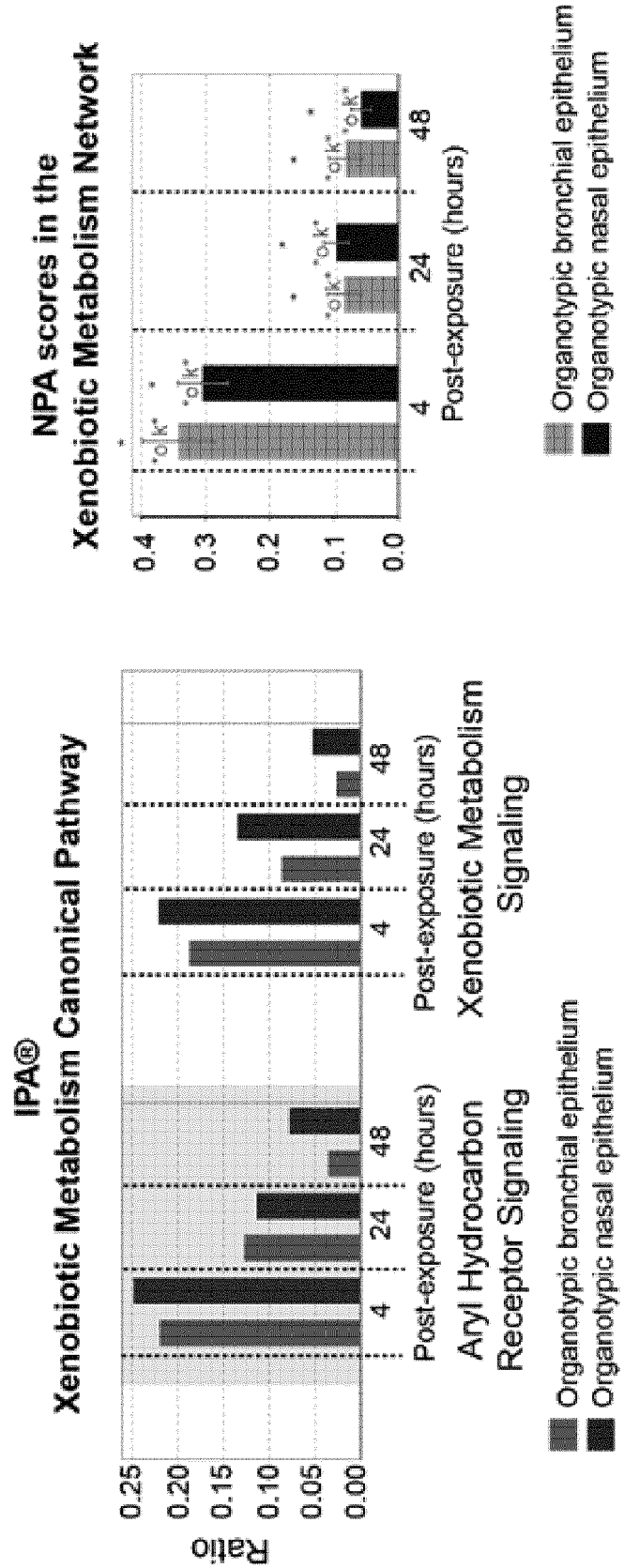
FIG. 7D depicts bar plots of network perturbation amplitude scores.

FIG. 7D shows the bar plot of NPA scores, which shows the statistical significance of the perturbation of the xenobiotic metabolism network model in response to smoking. The symbol * indicates significance of NPA scores generated from the in vitro bronchial and nasal datasets as well as their companion statistics O* and K* (P-values <0.05). The reduced responses were also reflected from the analyses using IPA®; decreased associations between the datasets and the two IPA®'s canonical pathways were observed at the later time point of post-exposure (FIG. 7D). The results from IPA® analysis were in agreement to that observed in the NPA score (FIG. 7D), in which the later time point of post-exposure had lower xenobiotic responses.

This data suggests that the shorter post-exposure time, the more perturbed the xenobiotic metabolism in both bronchial and nasal. This observation is consistent with a previous study in which a transient induction of phase I xenobiotic metabolism enzymes (e.g. cyp1A1 and aldh3A1) is observed in CS-exposed lung tissues of Sprague-Dawley rats [Gebel S, Gerstmayer B, Kuhl P, Borlak J, Meurrens K, Müller T: The kinetics of transcriptomic changes induced by cigarette smoke in rat lungs reveals a specific program of defense, inflammation, and circadian clock gene expression. *Toxicological Sciences* 2006, 93(2):422-431.]. Furthermore, this could offer a likely explanation for why a better correlation of the differential network backbone values between the in vitro organotypic bronchial and nasal models at the shorter post-exposure time was observed (FIG. 7C).

In a fourth example, a correlation was observed between in vivo bronchial brushing data and in vitro organotypic bronchial and nasal data. In particular, it was examined whether in vitro organotypic models could reveal a similar xenobiotic response upon exposure to CS as compared to the xenobiotic response observed in vivo. To do this, it was determined whether the activity values of the backbone nodes generated from the in vivo datasets were nicely correlated to those from the in vivo. The NPA approach that quantifies the changes at the backbone levels (i.e., the differential network backbone values) may indicate the potential biological mechanisms that were perturbed upon exposure to CS exposure. Therefore, whether similar biological responses occurred in in vivo as compared to in in vitro models can be inferred from the correlation between the activity values of the backbone nodes.

Figure 8A:
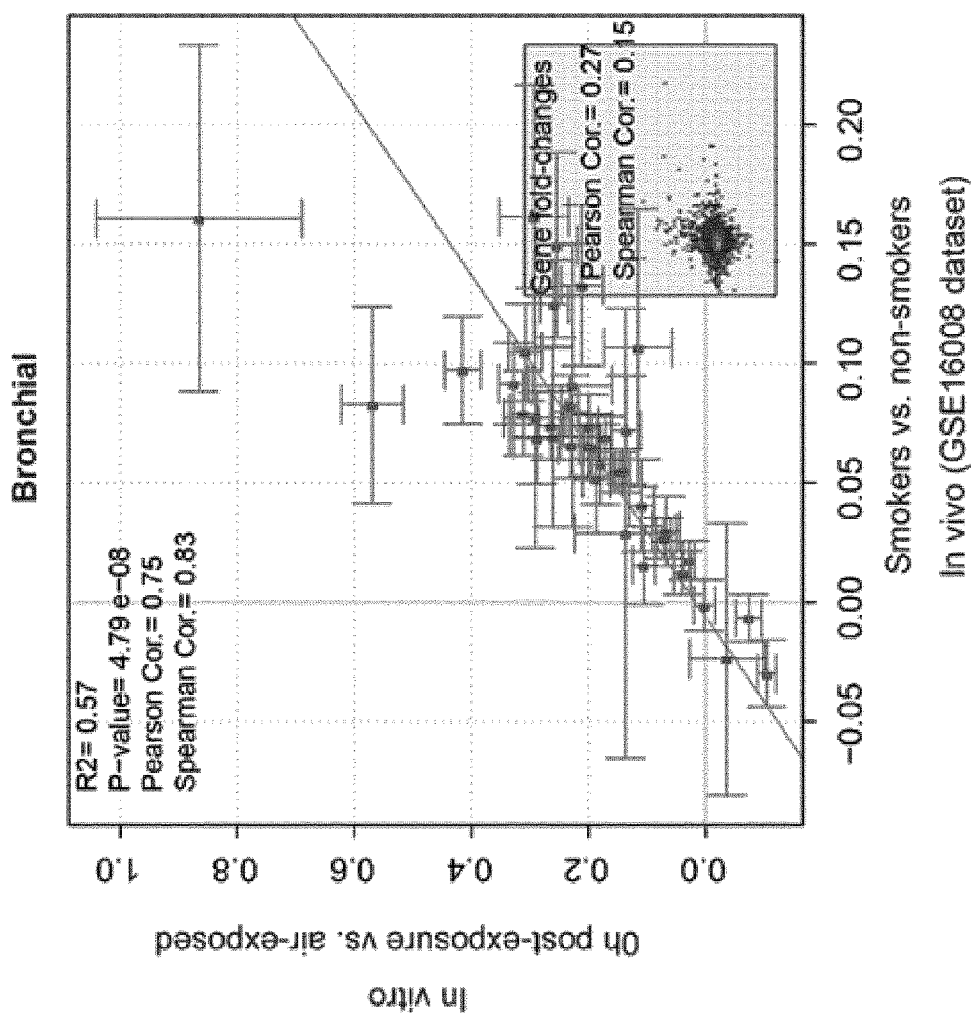
FIGS. 8A and 8B depict correlations between activity values at backbone nodes generated from in vivo data and activity values at backbone nodes generated from in vitro data, in bronchial and nasal samples.
Figure 8B:
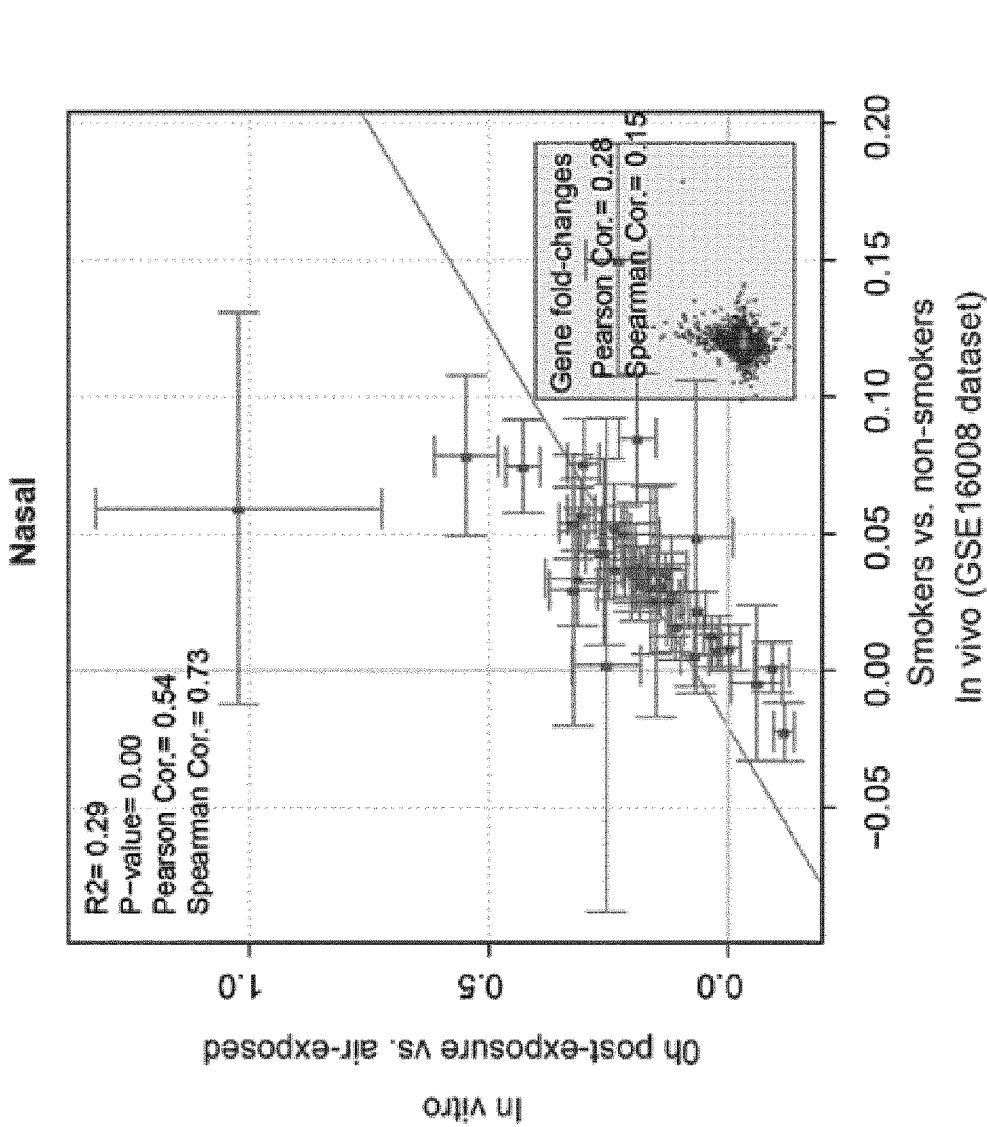
Figure 8C:
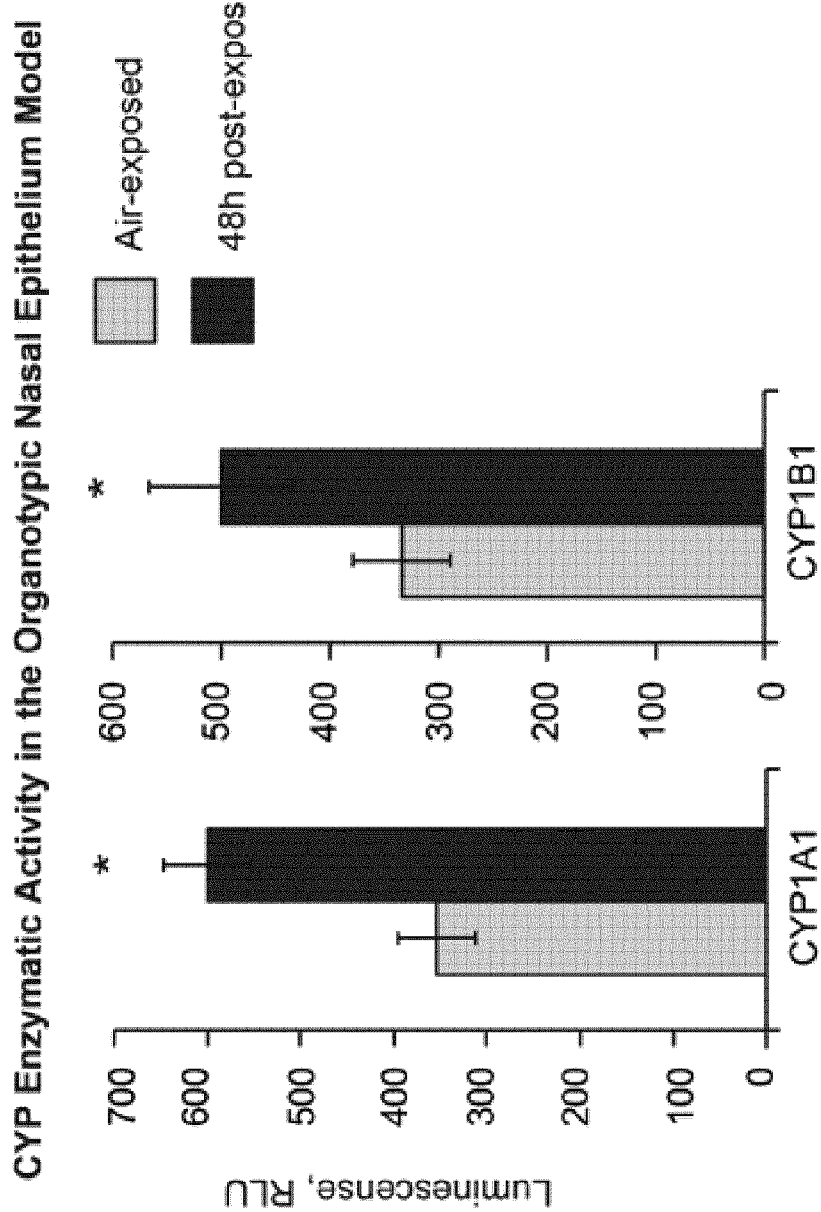
FIG. 8C depicts activities of CYP1A1 and CYP1B1 measured in a nasal epithelial model.
Figure 8D:
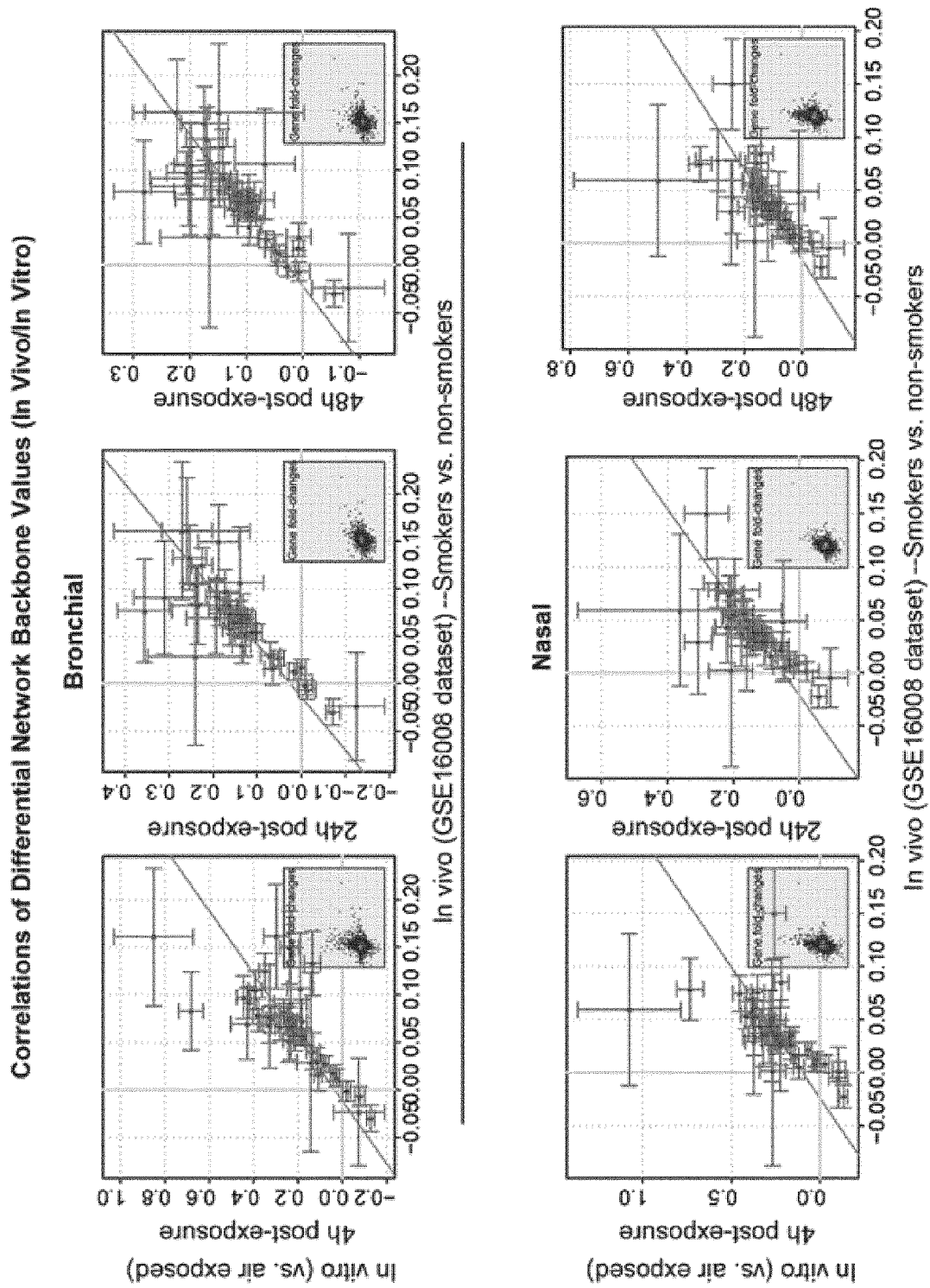
FIG. 8D depicts correlations between in vivo and in vitro data for differential network backbone values.

FIGS. 8A and 8B show the correlations between the activity values at the backbone nodes generated from in vivo dataset to those generated from in vitro models, in bronchial and nasal samples, respectively. These observations are consistent with an observation that a biological alteration in in vivo bronchial datasets was similar to an in vitro organotypic bronchial epithelial model (EpiAirway™ system, MatTeK Corporation) [Mathis C, Poussin C, Weisensee D, Gebel S, Hengstermann A, Sewer A, Belcastro V, Xiang Y, Ansari S, Wagner S: Human bronchial epithelial cells exposed in vitro to cigarette smoke at the air-liquid interface resemble bronchial epithelium from human smokers. *American Journal of Physiology-Lung Cellular and Molecular Physiology* 2013.]. The data shown in FIGS. 8A and 8B further suggest that the in vitro organotypic nasal model would be useful to investigate the mechanisms that occur in the in vivo nasal system upon smoking or upon exposure to CS. Furthermore, the correlation is weaker for the nasal epithelium (FIG. 8B) than for the bronchial epithelium (FIG. 8A). This is consistent with a previous study that showed the effect of smoking is less pronounced in the nasal epithelium as compared to the bronchial epithelium [Zhang X, Sebastiani P, Liu G, Schembri F, Zhang X, Dumas Y M, Langer E M, Alekseyev Y, O'Connor G T, Brooks D R et al: Similarities and differences between smoking-related gene expression in nasal and bronchial epithelium. *Physiological genomics* 2010, 41(1):1-8.]

Moreover, to better assess the in vitro organotypic nasal model, the effects of exposure to CS on the enzymatic activity of CYP1A1 and CYP1B1 were tested. It was found that exposure to CS significantly increased the activity of both CYP1A1 and CY1B1 measured in nasal epithelial model (FIG. 8C), supporting the potential of the nasal model to be utilized for toxicity assessment against airborne exposure. Additionally, although the xenobiotic responses generated from the in vitro organotypic models at the later time of post-exposure were reduced (FIG. 8D), the differential network backbone values remained correlated as compared to those generated from the in vivo datasets. Table 4 lists the Pearson and Spearman correlation coefficients for the data shown in FIG. 8D. In particular, the data shown in Table 4 indicates that the xenobiotic responses were better correlated in the bronchial tissue (FIG. 8A) than in the nasal tissue (FIG. 8B). Table 4 further indicates that although the xenobiotic responses generated from the in vitro organotypic models at the later time of post-exposure were reduced, the differential network backbone values remained well correlated as compared to those generated from the in vivo data sets.

Each reference that is referred to herein is hereby incorporated by reference in its respective entirety.

While implementations of the disclosure have been particularly shown and described with reference to specific examples, it should be understood by those skilled in the art that various changes in form and detail may be made therein without departing from the scope of the disclosure as defined by the appended claims. The scope of the disclosure is thus indicated by the appended claims and all changes which come within the meaning and range of equivalency of the claims are therefore intended to be embraced.

TABLE 1

| Backbone Node | Measurable Node | Relationship |
| --- | --- | --- |
| Particulate Matter | exp(GPX1) | 1 |
| Particulate Matter | exp(SCARA3) | −1 |
| Particulate Matter | exp(XBP1) | −1 |
| Particulate Matter | exp(SOD1) | 1 |
| Particulate Matter | exp(SOD2) | 1 |
| Particulate Matter | exp(HMOX1) | 1 |
| Particulate Matter | exp(DDIT3) | 1 |
| Particulate Matter | exp(HSPA5) | 1 |
| Particulate Matter | exp(CYP2F1) | −1 |
| Particulate Matter | exp(CYP2E1) | −1 |
| Particulate Matter | exp(GSTP1) | −1 |
| Particulate Matter | exp(CYP1A1) | −1 |
| Particulate Matter | exp(GSTM3) | −1 |
| Particulate Matter | exp(NQO1) | −1 |
| 8-Methyl-IQX | exp(GCLM) | 1 |
| 8-Methyl-IQX | exp(GSTP1) | 1 |
| 8-Methyl-IQX | exp(BTRC) | 1 |
| 8-Methyl-IQX | exp(PLK1) | 1 |
| 8-Methyl-IQX | exp(GPX2) | 1 |
| 8-Methyl-IQX | exp(GSTM1) | 1 |
| 8-Methyl-IQX | exp(GSTA5) | 1 |
| 8-Methyl-IQX | exp(YWHAB) | 1 |
| 8-Methyl-IQX | exp(TOP2A) | 1 |
| 8-Methyl-IQX | exp(GPX3) | 1 |
| 8-Methyl-IQX | exp(BRCA1) | 1 |
| Diesel exhaust particles | exp(GSTP1) | 1 |
| Diesel exhaust particles | exp(MAP2K5) | 1 |
| Diesel exhaust particles | exp(HSPB1) | 1 |
| Diesel exhaust particles | exp(EXOC3) | 1 |
| Diesel exhaust particles | exp(MYC) | 1 |
| Diesel exhaust particles | exp(DDIT3) | 1 |
| Diesel exhaust particles | exp(CLK1) | −1 |
| Diesel exhaust particles | exp(HMGB2) | −1 |
| Diesel exhaust particles | exp(RUNX1) | 1 |
| Diesel exhaust particles | exp(HMOX1) | 1 |
| Diesel exhaust particles | exp(KLF6) | 1 |
| Diesel exhaust particles | exp(IFRD1) | 1 |
| Diesel exhaust particles | exp(DNAJB1) | 1 |
| Diesel exhaust particles | exp(CDKN1A) | 1 |

TABLE 1-continued

| Backbone Node | Measurable Node | Relationship |
| --- | --- | --- |
| Diesel exhaust particles | exp(NQO1) | 1 |
| Diesel exhaust particles | exp(THBD) | 1 |
| Diesel exhaust particles | exp(TNFRSF1B) | 1 |
| Diesel exhaust particles | exp(HSPH1) | 1 |
| Diesel exhaust particles | exp(GSTA1) | 1 |
| Diesel exhaust particles | exp(CLU) | 1 |
| Diesel exhaust particles | exp(PCNA) | 1 |
| Diesel exhaust particles | exp(STMN1) | −1 |
| Diesel exhaust particles | exp(HSPA1B) | 1 |
| Diesel exhaust particles | exp(TGM2) | −1 |
| Diesel exhaust particles | exp(SERPINH1) | 1 |
| Diesel exhaust particles | exp(TRIB3) | 1 |
| Diesel exhaust particles | exp(CCND1) | 1 |
| Diesel exhaust particles | exp(BTG2) | 1 |
| Diesel exhaust particles | exp(PLAUR) | 1 |
| Diesel exhaust particles | exp(PTMA) | 1 |
| Diesel exhaust particles | exp(NME1) | 1 |
| Diesel exhaust particles | exp(NR4A3) | 1 |
| Diesel exhaust particles | exp(PRDX1) | −1 |
| Diesel exhaust particles | exp(ITGB7) | 1 |
| Diesel exhaust particles | exp(FOSL1) | 1 |
| Diesel exhaust particles | exp(CYP1A1) | 1 |
| Diesel exhaust particles | exp(KLF4) | 1 |
| Diesel exhaust particles | exp(MMP9) | 1 |
| Diesel exhaust particles | exp(AZI2) | 1 |
| Diesel exhaust particles | exp(SOD1) | 1 |
| Diesel exhaust particles | exp(KRAS) | 1 |
| Diesel exhaust particles | exp(BBOX1) | −1 |
| Diesel exhaust particles | exp(PRDX2) | 1 |
| Diesel exhaust particles | exp(ARAF) | 1 |
| Diesel exhaust particles | exp(VEGFA) | 1 |
| Diesel exhaust particles | exp(ADM) | 1 |
| Diesel exhaust particles | exp(CD36) | −1 |
| Diesel exhaust particles | exp(HBEGF) | 1 |
| Diesel exhaust particles | exp(LPXN) | 1 |
| Diesel exhaust particles | exp(PRKACB) | −1 |
| Diesel exhaust particles | exp(CYP1B1) | 1 |
| Diesel exhaust particles | exp(TGFB1) | 1 |
| Diesel exhaust particles | exp(TNFRSF12A) | 1 |
| Diesel exhaust particles | exp(RB1) | 1 |
| Diesel exhaust particles | exp(OSGIN1) | 1 |
| Diesel exhaust particles | exp(BAG3) | 1 |
| Diesel exhaust particles | exp(ATF3) | 1 |
| Diesel exhaust particles | exp(IL7) | 1 |
| Diesel exhaust particles | exp(IL1B) | 1 |
| Diesel exhaust particles | exp(SERPINB2) | 1 |
| Diesel exhaust particles | exp(HRH1) | 1 |
| Indirubin | exp(GPX1) | −1 |
| Indirubin | exp(NPC1) | 1 |
| Indirubin | exp(GSTP1) | 1 |
| Indirubin | exp(CAT) | −1 |
| Indirubin | exp(MT2A) | −1 |
| Indirubin | exp(CYR61) | 1 |
| Indirubin | exp(CLK1) | −1 |
| Indirubin | exp(BCL2L1) | 1 |
| Indirubin | exp(HMOX1) | −1 |
| Indirubin | exp(JUP) | −1 |
| Indirubin | exp(CDH2) | −1 |
| Indirubin | exp(TOP2A) | −1 |
| Indirubin | exp(CDKN1A) | 1 |
| Indirubin | exp(UNG) | 1 |
| Indirubin | exp(NQO1) | 1 |
| Indirubin | exp(COPS2) | −1 |
| Indirubin | exp(E2F1) | −1 |
| Indirubin | exp(NFKBIA) | 1 |
| Indirubin | exp(TOP1) | −1 |
| Indirubin | exp(EPHX2) | −1 |
| Indirubin | exp(MGST2) | −1 |
| Indirubin | exp(CCND3) | −1 |
| Indirubin | exp(SEPT2) | −1 |
| Indirubin | exp(PTGS2) | 1 |
| Indirubin | exp(HSPD1) | −1 |
| Indirubin | exp(MSH2) | −1 |
| Indirubin | exp(ARF4) | −1 |
| Indirubin | exp(GSR) | 1 |
| Indirubin | exp(ITGB1) | −1 |
| Indirubin | exp(CCNE1) | −1 |
| Indirubin | exp(ACADSB) | −1 |

TABLE 1-continued

| Backbone Node | Measurable Node | Relationship |
|---|---|---|
| Indirubin | exp(SERPINE1) | 1 |
| Indirubin | exp(HSBP1) | −1 |
| Indirubin | exp(ILF2) | −1 |
| Indirubin | exp(IL1R1) | −1 |
| Indirubin | exp(CCT4) | −1 |
| Indirubin | exp(HSPA6) | −1 |
| Indirubin | exp(TCF12) | −1 |
| Indirubin | exp(NFE2L2) | 1 |
| Indirubin | exp(CYP1A1) | 1 |
| Indirubin | exp(SOD2) | −1 |
| Indirubin | exp(CDKN1B) | 1 |
| Indirubin | exp(CDC2) | −1 |
| Indirubin | exp(HSPH1) | −1 |
| Indirubin | exp(SLC2A2) | −1 |
| Indirubin | exp(CCL4) | −1 |
| Indirubin | exp(RAD23A) | −1 |
| Indirubin | exp(BAX) | −1 |
| Indirubin | exp(CYP1B1) | 1 |
| Indirubin | exp(CCR4) | −1 |
| Indirubin | exp(CASP8) | 1 |
| AHR | exp(TFDP2) | 1 |
| AHR | exp(CYP2B6) | −1 |
| AHR | exp(AHRR) | 1 |
| AHR | exp(RAB9A) | 1 |
| AHR | exp(VAV3) | 1 |
| AHR | exp(MYC) | 1 |
| AHR | exp(RAB8A) | −1 |
| AHR | exp(ABR) | 1 |
| AHR | exp(CYP1B1) | 1 |
| AHR | exp(ARHGAP18) | −1 |
| AHR | exp(PCNA) | 1 |
| AHR | exp(SOS1) | 1 |
| AHR | exp(RFC3) | 1 |
| AHR | exp(NET1) | 1 |
| AHR | exp(TGFB1) | −1 |
| AHR | exp(RAB1A) | 1 |
| AHR | exp(ARHGAP20) | −1 |

TABLE 2

| Source Node | Relationship Type | Target Node |
|---|---|---|
| catof(CYP1A1) | -> | Reactive Oxygen Species |
| taof(AHR) | -> | NQO1 |
| taof(NR1I2) | -> | CYP1A1 |
| catof(ALDH3A1) | -\| | 4-Hydroxy-2-nonenal |
| Diesel exhaust particles | -> | Reactive Oxygen Species |
| Soot | -> | taof(AHR) |
| taof(AHR) | => | CYP1A1 |
| Polycyclic Aromatic Hydrocarbons | -sub-> | Benzpyrene |
| taof(NFE2L2) | -> | ALDH3A1 |
| catof(CYP1A2) | -> | Reactive Oxygen Species |
| 2,3,7,8-Tetrachlorodibenzodioxin | -> | catof(CYP1A1) |
| ESR1 | -e-> | taof(ESR1) |
| NQO1 | -> | GSTP1 |
| CYP1B1 | -cat-> | catof(CYP1B1) |
| catof(GSTP1) | -\| | 4-Hydroxy-2-nonenal |
| CYP1A1 | -cat-> | catof(CYP1A1) |
| AHRR | -\| | taof(AHR) |
| BRCA1 | -> | taof(NFE2L2) |
| Diesel exhaust particles | -> | taof(AHR) |
| Diesel exhaust particles | -> | catof(CYP1B1) |
| taof(ESR1) | => | CYP1B1 |
| Benzpyrene | -> | NQO1 |
| Polycyclic Aromatic Hydrocarbons | -> | catof(CYP1B1) |
| AHRR | =\| | taof(ESR1) |
| NR1I2 | -e-> | taof(NR1I2) |
| Indirubin | -> | taof(AHR) |
| taof(NR1I3) | -> | CYP1A1 |
| Benzpyrene | => | taof(AHR) |
| Benzpyrene | -> | TP53 |
| ALDH3A1 | -cat-> | catof(ALDH3A1) |
| 2,3,7,8-Tetrachlorodibenzodioxin | -> | CYP1A1 |
| CYP1A2 | -cat-> | catof(CYP1A2) |
| 8-Methyl-IQX | -> | taof(AHR) |
| 2,3,7,8-Tetrachlorodibenzodioxin | -> | CYP1B1 |
| taof(ESR1) | -> | CYP1A1 |
| NFE2L2 | -e-> | taof(NFE2L2) |
| taof(AHR) | -> | CYP1B1 |
| taof(NR1I2) | -> | CYP1A2 |
| Particulate Matter | -> | taof(AHR) |
| Curcumin | -\| | catof(CYP1A1) |
| 2,3,7,8-Tetrachlorodibenzodioxin | -> | catof(CYP1B1) |
| taof(AHR) | -> | ALDH3A1 |
| catof(CYP1B1) | -> | Reactive Oxygen Species |
| Particulate Matter | -sub-> | Polycyclic Aromatic Hydrocarbons |
| Polycyclic Aromatic Hydrocarbons | -> | taof(AHR) |
| catof(NQO1) | -\| | Reactive Oxygen Species |
| taof(AHR) | => | CYP1A2 |
| Reactive Oxygen Species | -> | 4-Hydroxy-2-nonenal |
| Polycyclic Aromatic Hydrocarbons | -> | catof(CYP1A1) |
| Particulate Matter | -sub-> | Soot |
| Nicotine | -> | CYP1A1 |
| BRCA1 | =\| | taof(ESR1) |
| Curcumin | -\| | catof(CYP1A2) |
| taof(AHR) | -> | AHRR |
| oxof(CYP2E1) | -> | Reactive Oxygen Species |
| AHR | -e-> | taof(AHR) |
| Diesel exhaust particles | -> | catof(CYP1A1) |
| taof(NFE2L2) | -> | NQO1 |
| GSTP1 | -cat-> | catof(GSTP1) |
| NR1I3 | -e-> | taof(NR1I3) |
| taof(AHR) | -> | NFE2L2 |
| Diesel exhaust particles | -> | taof(NFE2L2) |
| NQO1 | -cat-> | catof(NQO1) |
| Diesel exhaust particles | -> | catof(CYP1A2) |

Legend for Table 2

| | |
|---|---|
| -> | Increases |
| => | Directly Increases |
| -\| | Decreases |
| =\| | Directly Decreases |
| -sub-> | Target node is subset of source node |
| -cat-> | Target node represents catalytic activity of source node |
| -e-> | Target node represents transcriptional activity of the source node |

TABLE 3

| Comparison Group | Between the Backbone Values | | Between the Fold-change of Genes Expression | |
|---|---|---|---|---|
| | Pearson Correlation | Spearman Correlation | Pearson Correlation | Spearman Correlation |
| Bronchial in vitro vs. nasal in vitro (4 h post-exposure) | 0.97 | 0.95 | 0.72 | 0.55 |

TABLE 3-continued

| Comparison Group | Between the Backbone Values | | Between the Fold-change of Genes Expression | |
|---|---|---|---|---|
| | Pearson Correlation | Spearman Correlation | Pearson Correlation | Spearman Correlation |
| Bronchial in vitro vs. nasal in vitro (24 h post-exposure) | 0.93 | 0.94 | 0.62 | 0.49 |
| Bronchial in vitro vs. nasal in vitro (48 h post-exposure) | 0.77 | 0.86 | 0.39 | 0.37 | p-values <0.05 for all comparisons

TABLE 4

| Comparison Group | Between the Backbone Values | | Between the Fold-change of Genes Expression | |
|---|---|---|---|---|
| | Pearson Correlation | Spearman Correlation | Pearson Correlation | Spearman Correlation |
| Bronchial | | | | |
| In vivo vs. 4 h post-exposure in vitro | 0.73 | 0.77 | 0.25 | 0.13 |
| In vivo vs. 24 h post-exposure in vitro | 0.81 | 0.83 | 0.37 | 0.29 |
| In vivo vs. 48 h post-exposure in vitro | 0.77 | 0.80 | 0.35 | 0.30 |
| Nasal | | | | |
| In vivo vs. 4 h post-exposure in vitro | 0.57 | 0.76 | 0.35 | 0.27 |
| In vivo vs. 24 h post-exposure in vitro | 0.71 | 0.74 | 0.31 | 0.09 |
| In vivo vs. 48 h post-exposure in vitro | 0.65 | 0.73 | 0.26 | 0.14 | p-values <0.05 for all comparisons

The invention claimed is:

1. A computerized method for assessing perturbation of a target biological tissue of mammalian origin caused by exposure to an agent, comprising:
  (a) receiving, by at least one processor, data representative of a computational causal network model of xenobiotic metabolism, wherein the computational causal network model comprises measurable nodes and backbone nodes connected by edges, the backbone nodes and measurable nodes each representing a biological activity related to xenobiotic metabolism, and the edges representing causal relationships between the measureable nodes and backbone nodes, and wherein the computational causal network model represents the target biological tissue and a surrogate biological tissue;
  (b) receiving, by the at least one processor, a set of contrast data comprising activity measures for a portion of the measurable nodes, wherein the activity measures correspond to differences between treatment data and control data, wherein the treatment data is obtained from a first sample of the surrogate biological tissue that is exposed to the agent and the control data is obtained from a second sample of the surrogate biological tissue that is exposed to a control;
  (c) computing, by the at least one processor, a set of activity values for a portion of the backbone nodes based on the activity measures using the computational causal network model;
  (d) computing, by the at least one processor, a first score that indicates a perturbation of the first sample of the surrogate biological tissue that is exposed to the agent based on the set of activity values;
  (e) identifying, by the at least one processor, a correlation between the first sample of the surrogate biological tissue and a sample of the target biological tissue, wherein the sample of the target biological tissue comprises epithelial cells of a lower respiratory tract and the first sample of the surrogate biological tissue comprises epithelial cells of an upper respiratory tract; and
  (f) computing, by the at least one processor, a second score that indicates the perturbation of the target biological tissue in response to exposure to the agent based on the first score and the identified correlation.

2. The method of claim 1, further comprising:
  measuring expression levels of genes corresponding to the measurable nodes, the expression levels being the activity measures of the measurable nodes.

3. The method of claim 1, wherein the identifying the correlation further comprises:
  identifying the correlation between the set of activity values for the backbone nodes obtained from the surrogate biological tissue and a second set of activity values for the backbone nodes obtained from the target biological tissue, wherein the second set of activity values for the backbone nodes obtained from the target biological tissue is obtained in previously performed correlation experiments.

4. The method of claim 1, wherein the perturbation of the sample of the target biological tissue occurs in vivo, the first sample of the surrogate biological tissue is an in vitro cultures of cells of the sample of the target biological tissue, and the in vitro culture of cells of the sample of the target biological tissue is an organotypic culture.

5. The method of claim 1, wherein the sample of the target biological tissue comprises epithelial cells selected from the group consisting of: epithelial cells from lung, bronchus, primary bronchi, secondary bronchi, tertiary bronchi, bronchioles, trachea, nasal cavity, buccal cavity, and gingiva.

6. The method of claim 1, wherein the first sample of the surrogate biological tissue comprises epithelial cells selected from the group consisting of epithelial cells from lung, bronchus, primary bronchi, secondary bronchi, tertiary bronchi, bronchioles, trachea, nasal cavity, buccal cavity, and gingiva.

7. The method of claim 1, wherein the sample of the target biological tissue is more difficult to obtain than the first sample of the surrogate biological tissue due to its anatomical location being deeper inside the body.

8. The method of claim 1, further comprising:
  using the identified correlation to-correlate the set of activity values for the portion of the backbone nodes obtained from the first sample of the surrogate biological tissue to infer a set of activity values that indicates perturbation of the target biological tissue.

9. The method of claim 1, wherein the first score is a network perturbation amplitude (NPA) score, score provided by ingenuity pathway analysis (IPA), or score provided by gene set enrichment analysis (GSEA).

10. The method of claim 1, wherein the agent is selected from the group consisting of: an aerosol produced by heating or combusting tobacco, cigarette smoke, carbon monoxide, soot, diesel exhaust matter, particulate matters, and urban air pollutants.

11. The method of claim 1, wherein the identifying the correlation further comprises:
determining that the computational causal network model of xenobiotic metabolism is applicable to both the perturbation of the target biological tissue in response to the agent and the perturbation of the surrogate biological tissue in response to the agent.

12. The method of claim 1, wherein the computing the second score comprises scaling the first score by a scalar factor determined from the identified correlation.

13. The method of claim 1, wherein the agent includes cigarette smoke or an aerosol produced by heating or combusting tobacco, the surrogate biological tissue is sampled from nasal tissue, and the target biological tissue is lung tissue.

14. The method of claim 1, wherein the second score is a quadratic function of the activity measures for the portion of the measurable nodes.

15. A system for assessing perturbation of a target biological tissue of mammalian origin caused by exposure to an agent, comprising:
one or more communications ports configured to receive
(a) data representative of a computational causal network model of xenobiotic metabolism, wherein the computational causal network model comprises measurable nodes and backbone nodes connected by edges, the backbone nodes and measurable nodes each representing a biological activity related to xenobiotic metabolism, and the edges representing a causal relationship between the measureable nodes and backbone nodes, and wherein the computational causal network model represents the target biological tissue and a surrogate biological tissue; and
(b) a set of contrast data comprising activity measures for a portion of the measurable nodes, wherein the activity measures correspond to differences between treatment data and control data, wherein the treatment data is obtained from a first sample of the surrogate biological tissue that is exposed to the agent, and the control data is obtained from a second sample of the surrogate biological tissue that is exposed to a control; and
a processor configured to:
(i) compute a set of activity values for a portion of the backbone nodes based on the activity measures using the computational causal network model;
(ii) compute a first score that indicates a perturbation of the first sample of the surrogate biological tissue that is exposed to the agent based on the set of activity values;
(iii) identify a correlation between the first sample of the surrogate biological tissue and a sample of the target biological tissue, wherein the sample of the target biological tissue comprises epithelial cells of a lower respiratory tract and the first sample of the surrogate biological tissue comprises epithelial cells of an upper respiratory tract; and
(iv) compute a second score that indicates the perturbation of the target biological tissue in response to exposure to the agent based on the first score and the identified correlation.

16. A computerized method for assessing perturbation of a target biological tissue of mammalian origin caused by exposure to an agent, comprising:
determining a set of scores that is indicative of a perturbation of the target biological tissue based on:
(a) a computational causal network model of xenobiotic metabolism in the target biological tissue and a surrogate biological tissue, the computational casual network model comprising measurable nodes and backbone nodes connected by edges, the backbone nodes and measurable nodes each representing a biological activity related to xenobiotic metabolism, the edges representing causal relationships between connected nodes, wherein an activity value of a respective backbone node is determined by activity measures of the measurable nodes that are connected to the respective backbone node, and wherein the computational causal network model represents the target biological tissue and the surrogate biological tissue; and
(b) a set of contrast data comprising differences between the activity measures of the measurable nodes obtained from a first sample of the surrogate biological tissue that is exposed to the agent, and the activity measures of the measurable nodes obtained from a second sample of the surrogate biological tissue that is exposed to a control, wherein the determining the set of scores comprises:
(i) computing, at a first processor, a set of values for the backbone nodes using the set of contrast data; wherein the set of values for the backbone nodes indicates a perturbation of the surrogate biological tissue caused by the agent;
(ii) identifying data representative of a correlation between the computed set of values for the backbone nodes obtained from the surrogate biological tissue and the set of scores that is indicative of a perturbation of the target biological tissue; and
(iii) modifying at least one score in the set of scores to generate a modified score, the modifying based on the identified data representative of the correlation.

* * * * *